(12) United States Patent
Grychowski et al.

(10) Patent No.: US 8,061,352 B2
(45) Date of Patent: *Nov. 22, 2011

(54) AEROSOL DELIVERY APPARATUS AND METHOD

(75) Inventors: Jerry R. Grychowski, Lake Zurich, IL (US); George Baran, London (CA); Martin P. Foley, London (CA)

(73) Assignee: Trudell Medical International, London, Ontario (CA)

( * ) Notice: Subject to any disclaimer, the term of this patent is extended or adjusted under 35 U.S.C. 154(b) by 166 days.

This patent is subject to a terminal disclaimer.

(21) Appl. No.: 11/745,872

(22) Filed: May 8, 2007

(65) Prior Publication Data

US 2007/0204864 A1   Sep. 6, 2007

Related U.S. Application Data

(63) Continuation of application No. 11/452,100, filed on Jun. 13, 2006, which is a continuation of application No. 10/803,426, filed on Mar. 18, 2004, now Pat. No. 7,080,643, which is a continuation of application No. 10/241,205, filed on Sep. 11, 2002, now Pat. No. 6,748,945, which is a continuation of application No. 09/168,132, filed on Oct. 7, 1998, now Pat. No. 6,612,303, which is a continuation of application No. 08/600,419, filed on Feb. 13, 1996, now Pat. No. 5,823,179.

(51) Int. Cl.
*A61M 11/00* (2006.01)
*A61M 15/00* (2006.01)

(52) U.S. Cl. ......... 128/200.21; 128/200.14; 128/200.18; 128/203.12; 128/204.14; 128/205.23; 239/338

(58) Field of Classification Search ............. 128/200.14, 128/200.21, 200.22, 203.12, 203.16, 204.17, 128/204.19, 205.23, 913

See application file for complete search history.

(56) References Cited

U.S. PATENT DOCUMENTS

| | | | |
|---|---|---|---|
| 1,742,740 A * | 1/1930 | Watters | ........................ 73/709 |
| 2,535,844 A | 12/1950 | Emerson | |
| 2,882,026 A | 4/1959 | Eichelman | |
| 2,951,644 A | 9/1960 | Mahon et al. | |
| 3,172,406 A | 3/1965 | Bird et al. | |

(Continued)

FOREIGN PATENT DOCUMENTS

AU   B-29969/89   8/1990

(Continued)

OTHER PUBLICATIONS

Notice of Allowability and Examiner-Initiated Interview Summary dated Aug. 6, 2009 for U.S. Appl. No. 11/452,100.

(Continued)

*Primary Examiner* — Justine Yu
*Assistant Examiner* — Clinton Ostrup
(74) *Attorney, Agent, or Firm* — Brinks Hofer Gilson & Lione

(57) ABSTRACT

An apparatus and method for indicating breathing cycle of a patient using an aerosol delivery device. In one aspect, an aerosol delivery device includes a visual indicator that is moveable in response to a patient's breathing cycle and is positioned away from an inspiration path of the aerosol. In another aspect, a method of cycling a visual indicator between a first position and a second position in response to a patient's breathing cycle is described.

20 Claims, 9 Drawing Sheets

U.S. PATENT DOCUMENTS

| | | |
|---|---|---|
| 3,269,665 A | 8/1966 | Cheney |
| 3,467,092 A | 9/1969 | Bird et al. |
| 3,490,697 A | 1/1970 | Best, Jr. |
| 3,580,249 A | 5/1971 | Takaoka |
| 3,584,621 A | 6/1971 | Bird et al. |
| 3,630,196 A | 12/1971 | Bird et al. |
| 3,658,059 A | 4/1972 | Steil |
| 3,664,337 A | 5/1972 | Lindsey et al. |
| 3,826,255 A | 7/1974 | Havstad et al. |
| 3,838,686 A | 10/1974 | Szekely |
| 3,874,379 A | 4/1975 | Enfield et al. |
| 3,903,884 A | 9/1975 | Huston et al. |
| 3,990,442 A | 11/1976 | Patneau |
| 4,093,124 A | 6/1978 | Morane et al. |
| 4,094,317 A | 6/1978 | Wasnich |
| 4,106,503 A | 8/1978 | Rosenthal et al. |
| 4,116,387 A | 9/1978 | Kremer, Jr. et al. |
| 4,139,128 A | 2/1979 | Ewald |
| 4,150,071 A | 4/1979 | Pecina |
| 4,183,361 A | 1/1980 | Russo |
| 4,198,969 A * | 4/1980 | Virag ............... 128/200.21 |
| 4,206,644 A | 6/1980 | Platt |
| 4,210,140 A | 7/1980 | James et al. |
| 4,210,155 A * | 7/1980 | Grimes .................. 600/540 |
| 4,251,033 A | 2/1981 | Rich et al. |
| 4,253,468 A | 3/1981 | Lehmbeck |
| 4,268,460 A | 5/1981 | Boiarski et al. |
| 4,291,688 A | 9/1981 | Kistler |
| 4,333,450 A | 6/1982 | Lester |
| 4,413,784 A | 11/1983 | Dea |
| 4,452,239 A * | 6/1984 | Malem ................ 128/200.17 |
| 4,456,179 A | 6/1984 | Kremer |
| 4,470,412 A | 9/1984 | Nowacki et al. |
| 4,484,577 A | 11/1984 | Sackner et al. |
| 4,508,118 A | 4/1985 | Toth |
| 4,509,688 A | 4/1985 | Gagne et al. |
| 4,588,129 A | 5/1986 | Shanks |
| 4,620,670 A | 11/1986 | Hughes |
| 4,622,968 A | 11/1986 | Persson |
| 4,627,432 A | 12/1986 | Newell et al. |
| 4,657,007 A | 4/1987 | Carlin et al. |
| 4,674,491 A | 6/1987 | Brugger et al. |
| 4,677,975 A | 7/1987 | Edgar et al. |
| 4,746,067 A | 5/1988 | Svoboda |
| 4,758,224 A | 7/1988 | Siposs |
| 4,792,097 A | 12/1988 | Kremer, Jr. et al. |
| 4,809,692 A | 3/1989 | Nowacki et al. |
| 4,832,015 A | 5/1989 | Nowacki et al. |
| 4,911,157 A | 3/1990 | Miller |
| 4,984,158 A | 1/1991 | Hillsman |
| 5,012,803 A | 5/1991 | Foley et al. |
| 5,012,804 A | 5/1991 | Foley et al. |
| 5,020,527 A | 6/1991 | Dessertine |
| 5,020,530 A | 6/1991 | Miller |
| 5,042,467 A | 8/1991 | Foley |
| 5,054,477 A | 10/1991 | Terada et al. |
| 5,054,478 A | 10/1991 | Grychowski et al. |
| 5,078,131 A | 1/1992 | Foley |
| 5,086,765 A | 2/1992 | Levine |
| 5,165,392 A | 11/1992 | Small |
| 5,167,506 A | 12/1992 | Kilis et al. |
| 5,170,782 A | 12/1992 | Kocinski |
| 5,241,954 A | 9/1993 | Glenn |
| 5,277,175 A | 1/1994 | Riggs et al. |
| 5,280,784 A | 1/1994 | Kohler |
| 5,299,565 A | 4/1994 | Brown |
| 5,301,662 A | 4/1994 | Bagwell et al. |
| 5,301,663 A | 4/1994 | Small, Jr. |
| 5,309,900 A | 5/1994 | Knoch et al. |
| 5,312,046 A | 5/1994 | Knoch et al. |
| 5,312,281 A | 5/1994 | Takahashi et al. |
| 5,318,015 A | 6/1994 | Mansson et al. |
| 5,333,106 A * | 7/1994 | Lanpher et al. ............ 600/538 |
| 5,337,926 A | 8/1994 | Drobish et al. |
| 5,349,947 A | 9/1994 | Newhouse et al. |
| 5,363,842 A | 11/1994 | Mishelevich et al. |
| 5,383,470 A | 1/1995 | Kolbly |
| 5,385,140 A | 1/1995 | Smith |
| 5,392,648 A | 2/1995 | Robertson |
| 5,398,714 A | 3/1995 | Price |
| 5,427,089 A | 6/1995 | Kraemer |
| 5,431,154 A | 7/1995 | Seigel et al. |
| 5,458,136 A | 10/1995 | Jaser et al. |
| 5,461,695 A | 10/1995 | Knoch |
| 5,479,920 A | 1/1996 | Piper et al. |
| 5,487,378 A | 1/1996 | Robertson et al. |
| 5,497,765 A | 3/1996 | Praud et al. |
| 5,505,192 A | 4/1996 | Samiotes et al. |
| 5,505,193 A | 4/1996 | Ballini et al. |
| 5,511,538 A | 4/1996 | Haber et al. |
| 5,511,539 A | 4/1996 | Lien |
| 5,515,842 A | 5/1996 | Ramseyer et al. |
| 5,520,166 A | 5/1996 | Ritson et al. |
| 5,522,380 A | 6/1996 | Dwork |
| 5,533,497 A | 7/1996 | Ryder |
| 5,533,501 A | 7/1996 | Denyer |
| 5,544,647 A | 8/1996 | Jewett et al. |
| 5,549,102 A | 8/1996 | Lintl et al. |
| 5,570,682 A | 11/1996 | Johnson |
| 5,582,162 A | 12/1996 | Petersson |
| 5,584,285 A | 12/1996 | Salter et al. |
| 5,598,839 A | 2/1997 | Niles et al. |
| 5,613,489 A | 3/1997 | Miller et al. |
| 5,617,844 A | 4/1997 | King |
| 5,622,162 A | 4/1997 | Johansson et al. |
| 5,630,409 A | 5/1997 | Bono et al. |
| 5,645,049 A | 7/1997 | Foley et al. |
| 5,687,912 A | 11/1997 | Denyer |
| 5,701,886 A | 12/1997 | Ryatt |
| 5,704,344 A | 1/1998 | Cole |
| 5,740,793 A | 4/1998 | Hodson et al. |
| 5,752,505 A | 5/1998 | Ohki et al. |
| 5,758,638 A | 6/1998 | Kreamer |
| 5,765,553 A | 6/1998 | Richards et al. |
| 5,792,057 A | 8/1998 | Rubsamen et al. |
| 5,803,078 A | 9/1998 | Brauner |
| 5,816,240 A | 10/1998 | Komesaroff |
| 5,823,179 A * | 10/1998 | Grychowski et al. .... 128/200.18 |
| 5,848,588 A | 12/1998 | Foley et al. |
| 5,865,172 A | 2/1999 | Butler et al. |
| 5,875,774 A | 3/1999 | Clementi et al. |
| 5,881,718 A | 3/1999 | Mortensen et al. |
| 5,899,201 A | 5/1999 | Schultz et al. |
| 5,937,852 A | 8/1999 | Butler et al. |
| 5,954,049 A | 9/1999 | Foley et al. |
| 5,988,160 A | 11/1999 | Foley et al. |
| 6,026,807 A | 2/2000 | Puderbaugh et al. |
| 6,039,042 A | 3/2000 | Sladek |
| 6,044,841 A | 4/2000 | Verdun et al. |
| 6,073,628 A | 6/2000 | Butler et al. |
| 6,116,233 A | 9/2000 | Denyer et al. |
| 6,116,239 A | 9/2000 | Volgyesi |
| 6,129,080 A | 10/2000 | Pitcher et al. |
| 6,131,568 A | 10/2000 | Denyer et al. |
| 6,176,237 B1 | 1/2001 | Wunderlich et al. |
| 6,179,164 B1 | 1/2001 | Fuchs |
| 6,223,745 B1 | 5/2001 | Hammarlund et al. |
| 6,237,589 B1 | 5/2001 | Denyer et al. |
| 6,253,767 B1 | 7/2001 | Mantz |
| 6,293,279 B1 | 9/2001 | Schmidt et al. |
| 6,338,443 B1 | 1/2002 | Piper |
| 6,345,617 B1 | 2/2002 | Engelbreth et al. |
| 6,435,177 B1 | 8/2002 | Schmidt et al. |
| 6,450,163 B1 | 9/2002 | Blacker et al. |
| 6,481,435 B2 | 11/2002 | Hochrainer et al. |
| 6,513,519 B2 | 2/2003 | Gallem |
| 6,543,448 B1 | 4/2003 | Smith et al. |
| 6,557,549 B2 | 5/2003 | Schmidt et al. |
| 6,578,571 B1 | 6/2003 | Watt |
| 6,584,971 B1 | 7/2003 | Denyer et al. |
| 6,595,203 B1 | 7/2003 | Bird |
| 6,606,992 B1 | 8/2003 | Schuler et al. |
| 6,612,303 B1 * | 9/2003 | Grychowski et al. .... 128/200.21 |
| 6,644,304 B2 | 11/2003 | Grychowski et al. |
| 6,679,250 B2 | 1/2004 | Walker et al. |
| 6,698,421 B2 | 3/2004 | Attolini |
| 6,708,688 B1 | 3/2004 | Rubin et al. |

| | | | |
|---|---|---|---|
| 6,748,945 B2 * | 6/2004 | Grychowski et al. ..... 128/200.21 | |
| 6,823,862 B2 | 11/2004 | McNaughton | |
| 6,848,443 B2 | 2/2005 | Schmidt et al. | |
| 6,857,427 B2 | 2/2005 | Ziegler et al. | |
| 6,883,517 B2 | 4/2005 | Halamish | |
| 6,885,684 B2 | 4/2005 | Ichino | |
| 6,904,908 B2 | 6/2005 | Bruce et al. | |
| 6,929,003 B2 | 8/2005 | Blacker et al. | |
| 6,994,083 B2 | 2/2006 | Foley et al. | |
| 7,013,896 B2 | 3/2006 | Schmidt | |
| 7,036,505 B2 | 5/2006 | Bacon et al. | |
| 7,051,731 B1 | 5/2006 | Rogerson | |
| 7,080,643 B2 * | 7/2006 | Grychowski et al. ..... 128/200.14 | |
| 7,131,439 B2 | 11/2006 | Blacker et al. | |
| 7,131,440 B2 | 11/2006 | Sonntag | |
| 7,201,165 B2 | 4/2007 | Bruce et al. | |
| 7,252,085 B2 | 8/2007 | Kunschir | |
| 7,255,106 B2 | 8/2007 | Gallem et al. | |
| 7,261,102 B2 | 8/2007 | Barney et al. | |
| 7,267,120 B2 | 9/2007 | Rustad et al. | |
| 7,270,123 B2 | 9/2007 | Grychowski et al. | |
| 7,404,400 B2 | 7/2008 | Lulla et al. | |
| 7,458,372 B2 | 12/2008 | Feiner et al. | |
| 7,559,322 B2 | 7/2009 | Foley et al. | |
| 7,568,480 B2 | 8/2009 | Foley et al. | |
| 7,634,995 B2 | 12/2009 | Grychowski et al. | |
| 7,748,385 B2 | 7/2010 | Lieberman et al. | |
| 7,758,886 B2 | 7/2010 | Jauernig et al. | |
| 2002/0020762 A1 | 2/2002 | Selzer et al. | |
| 2002/0104531 A1 | 8/2002 | Malone | |
| 2002/0157663 A1 | 10/2002 | Blacker et al. | |
| 2003/0136399 A1 | 7/2003 | Foley et al. | |
| 2003/0159694 A1 | 8/2003 | McNaughton | |
| 2005/0039741 A1 | 2/2005 | Gallem et al. | |
| 2005/0183718 A1 | 8/2005 | Wuttke et al. | |
| 2006/0011196 A2 | 1/2006 | Gallem et al. | |
| 2006/0157052 A1 | 7/2006 | Foley et al. | |
| 2007/0023036 A1 | 2/2007 | Grychowski et al. | |
| 2007/0204864 A1 | 9/2007 | Grychowski et al. | |
| 2007/0235028 A1 | 10/2007 | Bruce et al. | |
| 2008/0083407 A1 | 4/2008 | Grychowski et al. | |
| 2008/0257345 A1 | 10/2008 | Snyder et al. | |
| 2009/0272820 A1 | 11/2009 | Foley et al. | |

FOREIGN PATENT DOCUMENTS

| | | |
|---|---|---|
| DE | 2804852 A1 | 8/1978 |
| DE | 8703534 U1 | 8/1987 |
| DE | 199 02 847 C1 | 5/2000 |
| DE | 199 53 317 C1 | 2/2001 |
| EP | 0 281 650 A1 | 9/1988 |
| EP | 0 414 536 A2 | 2/1991 |
| EP | 0 281 650 B1 | 3/1992 |
| EP | 0 514 085 A1 | 11/1992 |
| EP | 0587380 | 3/1994 |
| EP | 0601 708 A2 | 6/1994 |
| EP | 0 641 570 A1 | 3/1995 |
| EP | 0 711 609 A3 | 10/1996 |
| EP | 0 587 380 B1 | 11/1997 |
| EP | 0 855 224 A2 | 7/1998 |
| EP | 0 855 224 A3 | 7/1999 |
| EP | 0601 708 B1 | 3/2000 |
| EP | 0 855 224 B1 | 5/2004 |
| EP | 0 938 906 B1 | 11/2005 |
| FR | 1 070 292 | 7/1954 |
| FR | 93306974.2 | 3/1993 |
| FR | 2 763 507 A1 | 11/1998 |
| GB | 497 530 | 12/1939 |
| GB | 675524 | 7/1952 |
| GB | 2 253 200 A | 9/1992 |
| GB | 2 299 512 A | 10/1996 |
| GB | 2 310 607 A | 9/1997 |
| WO | WO 88/03419 A1 | 5/1988 |
| WO | WO 90/09203 | 8/1990 |
| WO | WO 94/17753 A1 | 8/1994 |
| WO | WO 98/26828 A2 | 6/1998 |
| WO | WO 98/41265 A1 | 9/1998 |
| WO | WO 98/44974 | 10/1998 |
| WO | WO 99/40959 A1 | 8/1999 |
| WO | WO 99/53982 | 10/1999 |
| WO | WO 00/59565 | 10/2000 |
| WO | WO 02/24263 A2 | 3/2002 |

OTHER PUBLICATIONS

U.S. Appl. No. 11/712,547, filed Feb. 28, 2007 entitled "Visual Indicator for an Aerosol Medication Delivery Apparatus and System".

Product information excerpt, Boehringer Ingelheim, from web address: http://www.torpex.com/product_information/, Aug. 11, 2003 (4 pages).

Product Information, Boerhinger Ingelheim, "Introducing TORPEX™ (aerosol albuteral sulfate): The Ultimate Tool for Equine Inhalation Treatment", from website http://www.torpex.com/product_information/, Mar. 21, 2002, pp. 1-3.

International Search Report for international application No. PCT/IB03/01904, dated Oct. 1, 2003, 8 pages.

Office Action issued in U.S. Appl. No. 11/712,547 on Feb. 25, 2010, 20 pages.

PARI LC Plus Instructions for Use (GB), PARI GmbH, dated Jul. 2001.

Office Action issued in U.S. Appl. No. 11/712,547, mailed Aug. 27, 2010, 14 pages.

* cited by examiner

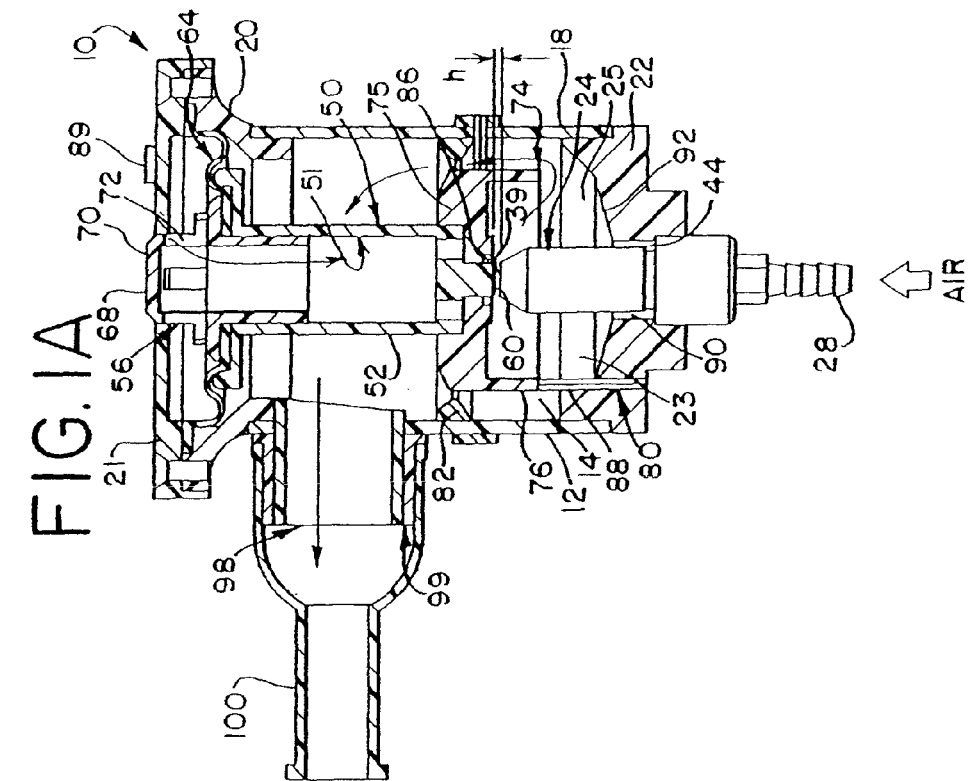
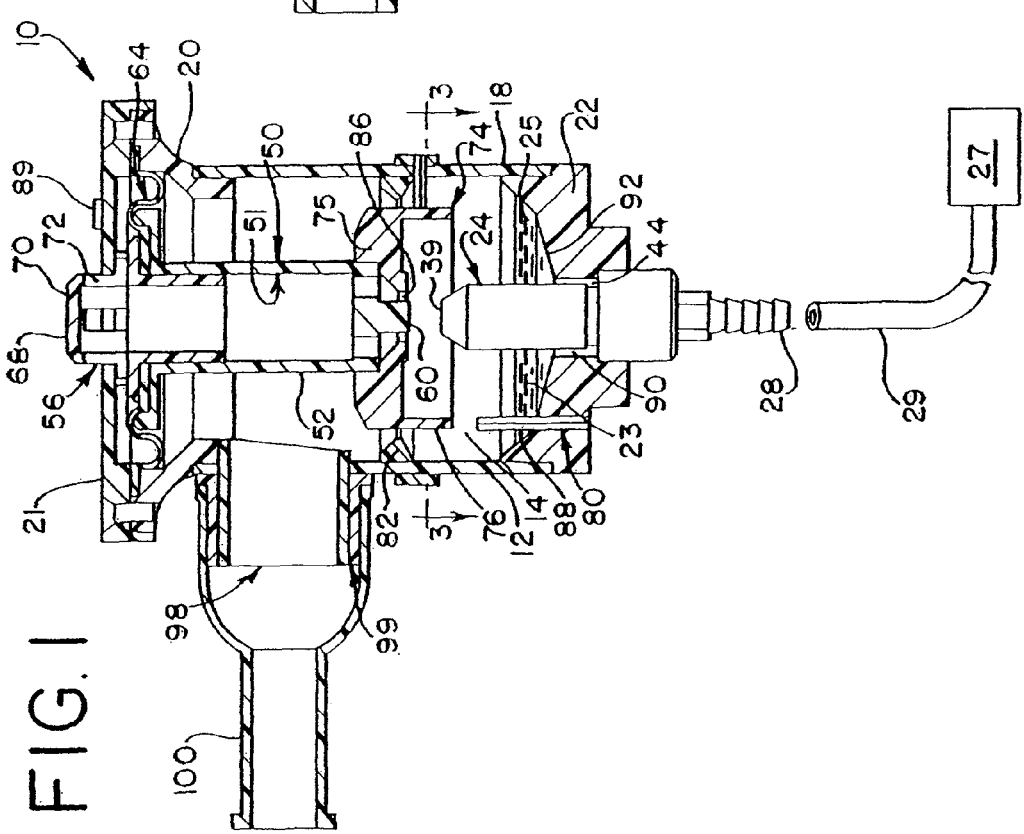

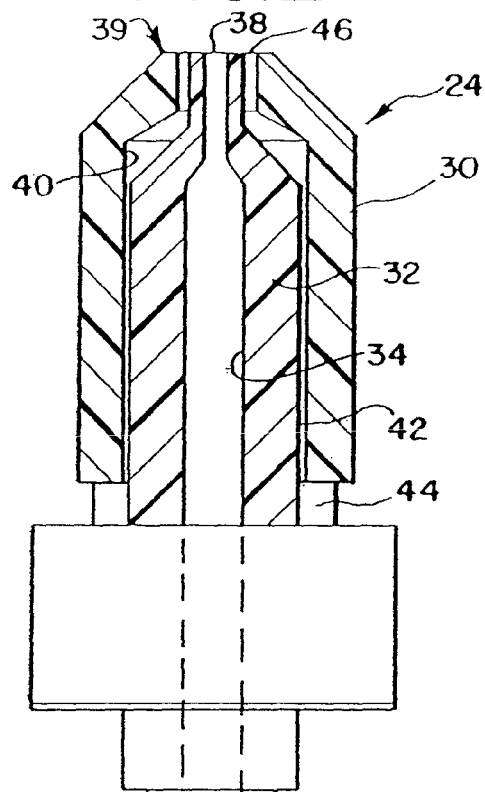
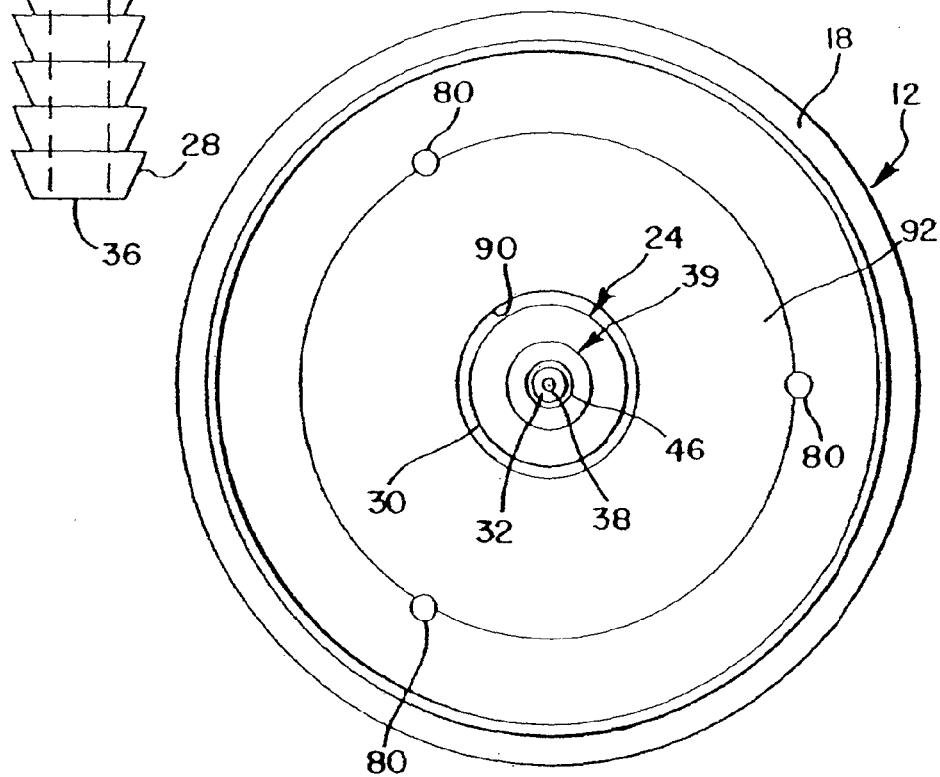

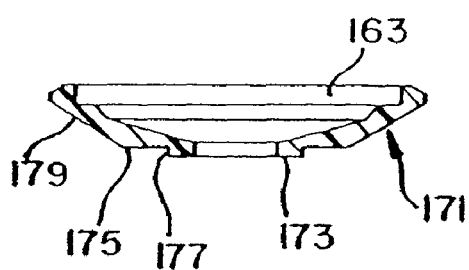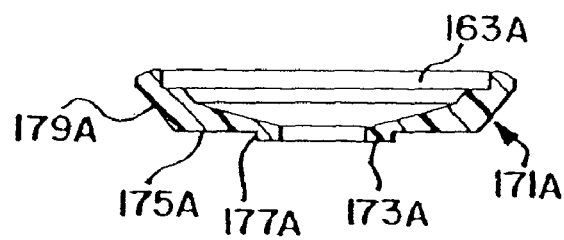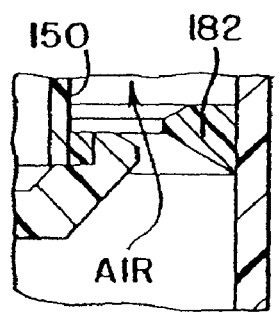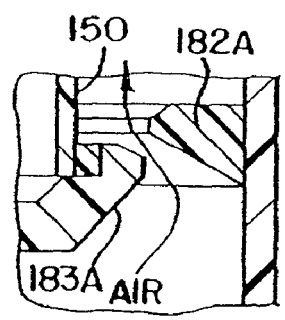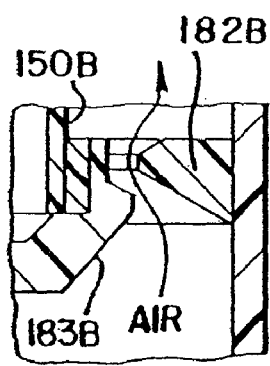

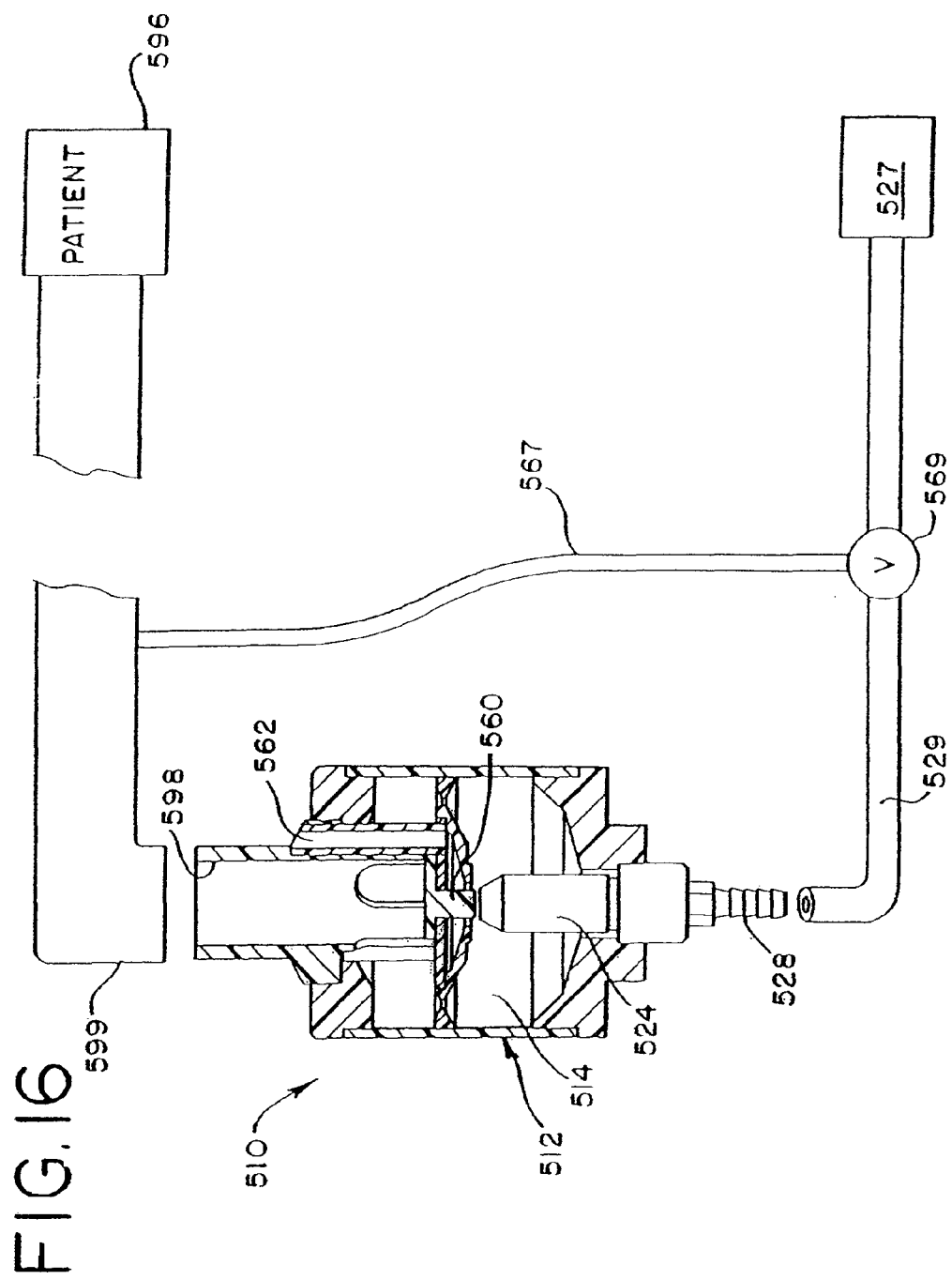

AEROSOL DELIVERY APPARATUS AND METHOD

CROSS-REFERENCE TO RELATED APPLICATIONS

This application is a continuation of U.S. application Ser. No. 11/452,100, filed Jun. 13, 2006, which is a continuation of U.S. application Ser. No. 10/803,426, filed Mar. 18, 2004, now U.S. Pat. No. 7,080,643, which is a continuation of U.S. application Ser. No. 10/241,205, filed Sep. 11, 2002, now U.S. Pat. No. 6,748,945, which is a continuation of U.S. application Ser. No. 09/168,132, filed Oct. 7, 1998, now U.S. Pat. No. 6,612,303, which is a continuation of U.S. application Ser. No. 08/600,419, filed Feb. 13, 1996, now U.S. Pat. No. 5,823,179, and the entire disclosure of each of these applications is incorporated herein by reference.

BACKGROUND

The present invention relates to a method and apparatus for delivering an aerosol, nebulized liquid or solid medicine or a vapor to a patient's respiratory tract, and more particularly, the present invention relates to an improved nebulizer that provides an aerosol more efficiently and with improved particle size uniformity.

Medical nebulizers for generating a fine spray or nebula of a liquid medicine that can be inhaled by a patient are well known devices commonly used for the treatment of certain conditions and diseases. Nebulizers have applications in treatments for conscious, spontaneously-breathing patients and for controlled ventilated patients.

In some nebulizers, a gas and a liquid are mixed together and directed against a baffle. As a result, the liquid is aerosolized, that is, the liquid is caused to form into small particles that are suspended in the air. This aerosol of the liquid can then be inhaled into a patient's respiratory tract. One way to mix the gas and liquid together in a nebulizer is to pass a quickly moving gas over a liquid orifice tip of a tube. The negative pressure created by the flow of pressurized gas is a factor that contributes to drawing the liquid out of the liquid orifice tip into the stream of gas and nebulize it.

Some of the considerations in the design and operation of nebulizers include regulation of dosages and maintenance of consistent aerosol particle size. In conventional nebulizer design, pressurized gas may entrain a liquid against a baffle on a continuous basis until the liquid in a reservoir is depleted. Continuous nebulization may result in a waste of aerosol during a patient's exhalation or during a delay between a patient's inhalation and exhalation. This effect may also complicate regulation of dosages because the amount of wasted aerosol may be difficult to quantify. Also, continuous nebulization may affect particle size and/or density. In addition, there may be excess medication lost to condensation on the nebulizer or mouthpiece during periods of non-inhalation. On the other hand, interrupted nebulization may also affect particle size and density as the nebulization is turned on and off.

There are several other considerations that relate to the effectiveness of nebulizer therapies. For example, it has been suggested that nebulization therapy is more effective when the generation of aerosol particles is relatively uniform, for example, producing particles of a particular size, particles within a range of sizes, and/or particles a substantial percentage of which are within a range of sizes. One particle size range that has been considered to be appropriate for inhalation therapy includes a particle size range of approximately 0.5 to 2 microns. Other particle size ranges may be suitable or preferable for particular applications. Generally, large and small size droplets should be minimized. It has also been considered desirable for some inhalation therapies that a substantial percentage, e.g. over 75%, of the aerosol particles be less than approximately 5 microns depending on the desired area of particle deposition in the respiratory tract. In addition, it may be advantageous for a nebulizer to be able to generate a large amount of aerosol quickly and uniformly so that a proper dosage can be administered.

Accordingly, with these considerations taken into account, there is a need for an improved nebulizer.

Other embodiments are disclosed, and each of the embodiments can be used alone or together in combination. Additional features and advantages of the disclosed embodiments are described in, and will be apparent from, the following Detailed Description and the figures.

BRIEF SUMMARY

The present disclosure provides a method and apparatus for delivering an aerosol to a patient. According to one aspect, an aerosol delivery apparatus includes a housing defining a chamber for holding an aerosol. An air inlet is in communication with the chamber and is configured to permit a flow of air into the chamber. An air outlet is also in communication with the chamber and is configured to permit the aerosol to be withdrawn from the chamber. An indicator may be operatively connected with the chamber and moveable in response to a breathing cycle of a patient, where the indicator comprises a visible characteristic and is positioned away from an inspiration path of the aerosol.

According to another aspect, an apparatus for aerosol delivery may include means for holding an aerosol and inlet means for permitting a flow of air into the means for holding the aerosol. The apparatus may also include outlet means for permitting the aerosol to be withdrawn from the means for holding the aerosol. Means for visually indicating a breathing cycle of a patient are operatively connected with the means for holding the aerosol and positioned away from an inspiration path of the aerosol.

According to still another aspect of the invention, a method is disclosed for delivering an aerosol from an aerosol delivery apparatus. The method includes supplying the aerosol to a chamber of the aerosol delivery apparatus and receiving a flow of air into the chamber during inhalation by a patient. Aerosol is supplied along an inspiration path in the aerosol delivery apparatus to an outlet in communication with the chamber during inhalation by the patient. The method also includes visually indicating a breathing cycle of the patient with an indicator that is associated with the aerosol delivery apparatus and positioned away from the inspiration path of the aerosol.

BRIEF DESCRIPTION OF THE DRAWINGS

FIG. 1 is a partial cross-sectional side view of a first embodiment of a nebulizer according to the present invention.

FIG. 1A is a cross-sectional view of the nebulizer of FIG. 1 shown in an inspiration cycle.

FIG. 2 is a cross-sectional view of the nozzle assembly of the nebulizer of FIG. 1.

FIG. 3 is a cross-sectional top view of the nebulizer of FIG. 1 taken along line 3-3' (without the baffle for clarity).

FIG. 6 is a cross sectional view of the bottom of the chimney of the embodiment of FIG. 5.

FIG. 7 is a cross sectional view similar to FIG. 6 showing an alternative embodiment the bottom of the chimney of the nebulizer shown in FIG. 5.

FIG. 8 is a cross-sectional view of a portion of the nebulizer of FIG. 5 showing the diverter ring.

FIG. 9 is a cross sectional view similar to FIG. 8 showing an alternative embodiment of the diverter ring arrangement for the embodiment of the nebulizer of FIG. 5.

FIG. 10 is a cross sectional view similar to FIG. 8 showing another alternative embodiment of the diverter ring arrangement.

FIG. 16 is a cross sectional view of a sixth embodiment of the nebulizer of the present invention.

Figure 4:
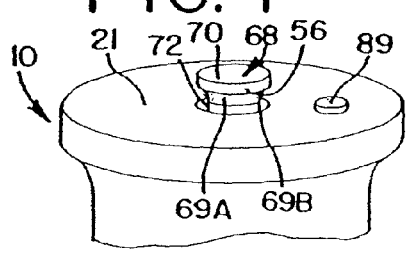
FIG. 4 is perspective view of the top portion of the nebulizer of FIG. 1.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

DETAILED DESCRIPTION OF THE DRAWINGS AND THE PRESENTLY PREFERRED EMBODIMENTS

I. First Embodiment

A first preferred embodiment of a nebulizer 10 is illustrated in FIG. 1. The nebulizer 10 is a small volume nebulizer and includes a housing or container 12 defining an internal chamber 14. The housing 12 is formed of a cylindrically-shaped side wall portion 18, a top portion 20, and a bottom portion 22. The component parts of the housing 12 may be formed of separate, multiple pieces of material that are connected together by welding, adhesives, etc., or more preferably, some of the component parts may be formed together of a single piece of material formed by an injection molding process. For example, the bottom, and side portions 22 and 18 may be formed of separate pieces that are connected together, or preferably, these parts may be formed of one piece of molded plastic. Any of a number of plastics may be suitable, including polycarbonate, or polycarbonate blends. A cover 21 is removably mounted on the upper portion of the housing 12, such as by means of a snap-on cover arrangement, twist-lock threads, screws or other types of fasteners. The housing 12 is approximately 6 cm (2.36 in) in height and has a diameter of approximately 4 cm (1.57 in).

A lower portion 23 of the chamber 14 serves as a reservoir for holding a fluid 25 for nebulizing, such as a solution containing a medication. Located in the lower portion 23 of the housing 12 is a nozzle assembly 24. Referring to FIGS. 1-3, the nozzle assembly 24 extends downward from the chamber 14 of the housing 12 to a fitting 28 located external of the chamber 14 on a bottom side 22 of the housing 12. The fitting 28 is sized to connect to a supply 27 of pressurized gas provided through conventional tubing 29. The pressurized gas may be supplied by any suitable source, such as a conventional gas supply used in hospitals, a pump, compressor, cartridge, canister, etc.

The nozzle assembly 24 is comprised of an outer tubular member 30 and an inner tubular member 32. The inner tubular member 32 has a passageway 34 that extends from an opening 36 in the bottom end of the fitting 28 to a gas outlet orifice 38 located at a top end 39 of the nozzle assembly 24. The inner tubular member 32 is located in an inner passageway 40 of the outer tubular member 30. The inner tubular member 32 is sized to slide into the inner passageway 40 of the outer tubular member 30 so that it is aligned therein. A passageway 42 is formed by grooves or slots on the outer surface of the inner tubular member 32 and/or the inner surface of the outer tubular member 30. The passageway 42 extends from a liquid reservoir opening 44 located at the reservoir 23 of the lower portion of the chamber 14 to a liquid outlet orifice 46 located at the top end 39 of the nozzle assembly 24. The passageway 42 serves to convey liquid medicine from the reservoir 23 at the bottom of the chamber 14 to the liquid outlet orifice 46 at the top of the nozzle assembly 24. (In an alternative embodiment, the passageway 42 may be formed by spaces or regions between fins located on the outer surface of the inner tubular member 32 and/or the inner surface of the outer tubular member 30.)

As shown in FIG. 3, the liquid outlet orifice 46 has an annular shape defined by the top ends of the outer tubular member 30 and the inner tubular member 32 of the nozzle assembly 24. The gas outlet orifice 38 has a circular shape and is located concentrically of the annular liquid orifice. In one embodiment, the gas outlet orifice 38 is approximately 0.022 inches in diameter and the liquid outlet orifice 46 has an outer diameter of approximately 0.110 to 0.125 inches and an inner diameter of approximately 0.084 inches. These dimensions are provided by way of example and the nebulizer may be made in other sizes with different dimensions as desired. The top end 39 of the nozzle assembly 24 is formed by the top ends of the outer and inner tubular members 30 and 32. In a present embodiment, the top end 39 is a generally flat surface having a diameter of approximately 0.18 inches. In alternative embodiments, the top end 39 may have an other-than-flat shape, for example, the inner tubular member 32 may be spaced above the outer tubular member 30 so that the liquid orifice 46 is located below the gas orifice 38.

The nozzle assembly 24, or a portion thereof, may be formed as part of the housing 12 as a single piece of material in an injection molding process. For example, the inner tubular member 32 may be formed of the same piece of injected molded plastic as the bottom of the housing 12. Referring again to FIG. 1, the nebulizer 10 also includes a chimney assembly 50. The chimney assembly 50 is located in an upper portion of the chamber 14 above the liquid reservoir 23. The chimney assembly 50 includes a tubular body 51 that defines an internal passageway 52 that extends from an inlet opening 56 in the housing cover 21 to a chimney outlet opening 58 at a bottom end of the tubular body 51. Thus, the chimney assembly 50 serves as an inlet channel for ambient air to enter into the chamber 14. The inlet opening 56 communicates with ambient air (through ports of an actuator button, as described below) and the chimney outlet opening 58 communicates with the chamber 14.

Located on the lower end of the chimney assembly 50 is a diverter 60. The diverter 60 may be formed of the same piece of molded plastic material as the chimney 50 or alternatively, the diverter 60 may be formed of a separate piece of material that is attached by suitable means to the rest of the chimney assembly 50. (The diverter may also be provided pneumatically, for example by an opposing gas source located directly opposite the nozzle.) The diverter 60 is located directly opposite from the gas outlet orifice 38 and the liquid outlet orifice 46 located at the top end 39 of the nozzle assembly 24. The diverter 60 is movable so that the distance between the diverter 60 and the top surface 39 of the nozzle assembly 24 can be varied. The diverter 60 has of a flat circular shape with a diameter of approximately 0.18 inches so that it extends over both the gas and liquid orifices 38 and 46 out to approximately the edge of the top surface 39 of the nozzle assembly 24. The chimney assembly 50 is connected to the housing 12. Specifically, the chimney assembly 50 is attached to the top portion 20 of the housing 12 by means of a membrane or diaphragm 64. The membrane 64 is a ring-shaped piece of a flexible, resilient material, such as silicone rubber. An outer rim or bead of the membrane 64 is secured in a groove in the top portion 20 of the housing 12 and/or the cover 21. An inner rim of the membrane 64 is secured in a slot formed by two parts of the chimney assembly 50. The membrane 64 has a rolled cross-sectional profile as shown in FIG. 1. This permits the membrane 64 to act as a rolling diaphragm. The membrane 64 permits limited movement of the chimney assembly 50. The chimney assembly 50 is connected to the membrane 64 so that the membrane 64 biases the chimney assembly 50 away from the nozzle assembly 24 as shown in FIG. 1. When installed in the manner shown in FIG. 1, the bottom of the chimney assembly 50 is approximately 0.15 inches away from the top surface of the nozzle assembly 24.

Located at the top end of the chimney assembly 50 is an actuator 68. The actuator 68 connects to the tubular body 51 of the chimney assembly 50 and extends through the opening 56 at the top of the housing 12 in the cover 21. The actuator 68 includes a closed top side 70 with one or more side opening ports 72.

Referring to FIG. 4, located on the sides of the body of the actuator 68 are indicators 69A and 69B. The indicators 69A and 69B may be formed of colored markings or parallel rings on the sides of the actuator 68. In a preferred embodiment, the indicator 69A is red and is located next to the top side 21 of the nebulizer body 12. The indicator 69B is preferably green and is adjacent to and above the indicator 69A.

Located in the chamber 14 at the bottom end of the chimney assembly 50 is a bell-shaped baffle 74. The baffle 74 extends from the opening 58 at the bottom of the chimney passageway 51 outward toward the inside wall of the cylindrical portion 18 of the housing 12. The baffle 74 includes a horizontal portion 75 and a vertical portion 76 that extends downward from the horizontal portion 75 toward the top of the nozzle assembly 24. The baffle 74 has an open bottom side providing an air passageway around the bottom side of the cylindrical vertical wall 76.

As mentioned above, the diverter 60 is movable relative to the nozzle assembly 24. The present embodiment provides a means to limit the travel of the diverter relative to the nozzle assembly 24. This may be accomplished in any of several suitable ways. In a present embodiment, the movement of the diverter 60 toward the nozzle assembly 24 is limited by one or more stop pins 80. The stop pins 80 extend up from the bottom portion 22 of the housing. In a present embodiment, there are three stop pins. The top ends of the stop pins 80 are spaced away from the bottom end of the vertical wall 76 of the baffle 74. Because the chimney assembly 50 is movable vertically due to its connection to the housing 12 by means of the flexible membrane 64, the stop pins 80 provide a lower limit to the movement of the chimney assembly 50. In a present embodiment, the stop pins 80 are spaced so that when the lower edge of the vertical wall 76 of the baffle 74 is brought into contact with the stop pins 80, a space 'h' is provided between the diverter 60 and the upper surface 39 of the nozzle assembly 24. In a preferred embodiment, the space 'h' is approximately between 0.025 and 0.045 inches, or more preferably approximately between 0.030 and 0.040 inches, and most preferably approximately 0.033 inches.

In alternative embodiments, movement of the diverter 60 toward the nozzle assembly 24 may be limited by means other than stop pins. For example, if the housing were formed by an injection molding process, steps, shoulders, fins, or other structures, may be provided along the walls of the housing in order to limit the downward travel of the chimney and/or diverter.

Also located in the chamber 14 is a diverting ring 82. The diverting ring 82 is located on the inner wall of the cylindrical portion 18 of the housing 12. Specifically, the diverting ring 82 is positioned adjacent to the baffle 74. The diverting ring 82 is sized to define a gap 86 around the baffle 74. The diverting ring 82 serves to impede large droplets of liquid that might form on the inner wall of the housing 12 and divert large droplets back down into the reservoir 23 at the bottom of the housing 12. In addition, the diverting ring 82 serves to provide a relatively tortuous path for the flow of aerosol particles from the lower portion of the chamber 14 to the upper portion. This tortuous path also serves to reduce the presence of larger particles and helps to make the particle size distribution more uniform.

As mentioned above, the bottom of the chamber 14 serves as a reservoir 23 for a liquid to be nebulized. In a present embodiment, the reservoir has a funnel-like shape to direct the liquid to be nebulized in a downward direction toward the inlet 44. The reservoir portion of the chamber 14 is formed of at least two portions or stages. In a present embodiment, an upper portion 88 of the reservoir is relatively wide having a diameter approximately the same as that of the cylindrical portion 18 of the housing 12 (e.g. 2.36 in). The upper portion 88 is relatively shallow (e.g. 0.3125-0.25 in). The upper portion 88 of the reservoir tapers in a funnel-like manner toward a lower portion 90 (or secondary well) of the reservoir. The lower portion 90 is relatively narrow, but relatively deep (e.g. 0.25 in). The lower portion 90 of the reservoir is slightly wider (e.g. 0.625 in) than the outer diameter of the nozzle assembly 24. The opening 44 from which the liquid is drawn is located at the bottom of the lower portion 90 of the reservoir. In a present embodiment, the reservoir 23 also includes an intermediate portion 92 located between the upper portion 88 and the lower portion 90. The intermediate portion 92 of the reservoir 23 has a height and a width between that of the upper and lower portions.

In the embodiment of the nebulizer shown in FIG. 1, the relative sizes and dimensions of the upper, lower and intermediate portions of the reservoir 23 contribute to the generation of an aerosol wherein the aerosol particle size and output is relatively uniform overall. As described more below, the liquid in the reservoir 23 is drawn through the opening 44 and up the liquid passageway 42 in part by the negative pressure caused by the flow of gas across the liquid orifice 46. The suction force provided by the gas flow both draws the liquid up out of the reservoir to the top of the nozzle and entrains the liquid with a certain velocity in the air flow. As the liquid is nebulized, the surface level of the liquid in the reservoir goes down, thereby directly increasing the distance that the liquid has to be drawn up out of the reservoir to the orifice at the top of the nozzle. As the distance of the top of the nozzle over the liquid surface increases, more energy is required to draw the liquid up to the liquid orifice at the top of the nozzle assembly 24. Assuming a relatively constant gas pressure, this increasing distance may have the effect of decreasing liquid flow through the liquid orifice which in turn may affect the uniformity of the aerosol particle size and rate.

The embodiment of the nebulizer in FIG. 1 reduces this possible adverse effect. With the embodiment of FIG. 1, a relatively large portion of the liquid is stored in the upper portion 88 of the reservoir and a relatively smaller portion of the liquid is stored in the lower portion 90 of the reservoir. Since the large portion 88 of the reservoir is wide and relatively shallow, the surface level of the liquid in the reservoir changes relatively slightly as the liquid in this portion of the reservoir is drawn down. Therefore, there is little change in the energy needed to draw this amount of liquid up from the reservoir to the liquid orifice 46 as this portion of the liquid is depleted. When all the liquid in the upper portion 88 of the reservoir is nebulized, the remaining liquid in the lower portion 90 of the reservoir is drawn into the liquid passageway 42 and the height of the top surface of the liquid falls rapidly. However, since the lower portion 90 of the reservoir is relatively narrow, it contains only a small portion of the liquid being nebulized so there is relatively little overall effect on aerosol particle size and output from this portion of the liquid.

Another advantage provided by the funnel shape of the reservoir is that the relatively narrow size of the lower portion 90 of the reservoir has less surface area thereby directing the liquid toward the opening 44. This causes most or all of the liquid to be directed to opening 44 with little waste.

The nebulizer 10 of FIGS. 1-3 may also include a sensor 89. The sensor 89 may be attached to the housing 12 at any suitable location, such as on the cover 21, as shown in FIG. 1. The sensor 89 monitors the operating cycles of the nebulizer 10. The sensor 89 may monitor operating cycles by monitoring the movement of the chimney portion 50 relative to the housing body 12. The sensor 89 may utilize any suitable technology, such as electronic, pneumatic, or mechanical. For example, the sensor may be responsive to a change in local capacitance as the chimney moves closer and further from the top of the housing. Alternatively, the sensor may be responsive to a embedded magnet, or may measure an optical parameter, etc. The sensor 89 monitors the cycles of operation and provides a count that can be observed by the user or a medical care provider. This enables the user or care provider to estimate how much medication has been delivered. The sensor 89 includes a display or similar device for this purpose. In addition, the sensor may also include appropriate programming to report on the duration, frequency, speed, etc. of nebulizer operation. These parameters may also be provided to inform the patient or care provider about the delivery of medication. This embodiment of the nebulizer may also include appropriate programming to limit the amount of medication or drugs that can be administered. For example, if the nebulizer is used to deliver drugs for pain control, such as morphine, the nebulizer can be programmed to limit the amount of such drugs that can be delivered to the patient.

The embodiment of the nebulizer shown in FIGS. 1-3 is adapted for use by a spontaneously breathing patient, so the aerosol from the nebulizer is output to a mouthpiece or mask that can be used by the spontaneously breathing patient. Accordingly, located in an upper portion of the chamber 14 is an adapter 99 having a chamber outlet 98 that connects to a mouthpiece 100. In alternative embodiments, as described further below, the nebulizer may be used with ventilator systems and instead of the mouthpiece 100, the adapter 99 would connect the outlet 98 to the ventilator circuit.

To operate the nebulizer 10, a suitable amount of a liquid such as a medicine or water is placed in the reservoir of the chamber 14. The liquid may be placed in the reservoir by first removing the cover 21, membrane 64, and chimney 50, filling an appropriate amount of liquid into the reservoir, and replacing the cover 21, membrane 64, and chimney 50 onto the housing 12. In a preferred embodiment, the cover, membrane and chimney are assembled together and would be removable together as a unit. (Alternatively, the liquid may be placed into the reservoir through the mouthpiece 100, or further, the nebulizer may be provided pre-filled with the appropriate amount of medicine from the manufacturer, or in yet another alternative, the nebulizer may be provided with a resealable fill port.) The source of pressurized gas 27 is connected to the fitting 28. The source of pressurized gas 27 may be an external source that provides gas at a rate of 4 to 10 liters per minute in a range from 35 p.s.i to 50 p.s.i, although other rates and pressures could also be suitable. Gas is delivered through the passageway 34 and is expelled from the gas outlet orifice 38 into the chamber 14. However, at this stage, prior to inhalation by the patient, the gas travels upward from the gas outlet orifice 38 and nebulization does not occur since the diverter 60 is in the non-nebulizing position. The membrane 64 holds the chimney assembly 50, including the diverter 60, away from the nozzle 24. When in the non-nebulizing position, the distance between the diverter 60 and the top of the nozzle is approximately 0.15 inches. At this distance, the gap between the diverter 60 and the nozzle 24 is such that the flow of gas does not create sufficient negative pressure over the liquid orifice 46 to draw out the liquid.

To generate an aerosol with the nebulizer, the patient places the mouthpiece 100 to his/her mouth. When the patient inhales, air is withdrawn from the chamber 14 reducing the pressure inside the housing 12. The lower pressure in the chamber 14 causes the membrane 64 to flex drawing the chimney 50 down. The lower position of the chimney 50 is shown in FIG. 1A. Downward movement of the chimney 50 is limited by the stop pins 80. When the stop pins 80 limit the downward movement of the chimney 50, the diverter 60 is spaced a predetermined distance 'h' from the top surface 39 of the nozzle assembly 24. In a present embodiment, the gap 'h' is approximately 0.033 inches.

The pressurized gas, which may be continuously injected into the nebulizer through the fitting 38, is diverted sideways approximately 90.degree. by the diverter 60. Since the gas outlet orifice 38, diverter 60 and nozzle top 39 are generally circular, gas exiting the orifice 38 is dispersed evenly in an approximately 360.degree. or radial pattern. The liquid medicine in the reservoir is then drawn up the passageway 42 and out of the liquid outlet orifice 46 in part by the negative pressure caused by the moving gas passing over the liquid outlet orifice. The liquid drawn into the diverted gas stream is aerosolized at least by the time it reaches the larger volume space of the chamber. In a present embodiment, the liquid medicine drawn out of the liquid orifice 46 has little or no impaction against the diverter 60. However, in an alternative embodiment, the liquid drawn into the gas stream may be directed against the diverter 60.

As the liquid is nebulized it travels into the chamber 14 along a path around the lower edge of the baffle 74. As the patient inhales, the nebulized liquid travels upward through the gap 86 between the baffle 74 and the diverting ring 82, and out through the mouthpiece 100 to the patient's respiratory tract.

When the patient ceases to inhale, the pressure in the chamber 14 rises. The biasing of the membrane 64 is again sufficient to move the chimney 50 upward, increasing the distance between the diverter 60 and the top surface 39 of the nozzle assembly 24, and causing nebulization of the liquid to cease. In alternative embodiments, a spring, pneumatic valve, or other biasing device may be utilized, alone or in combination with each other and the membrane, to move the diverter 60 into a non-nebulizing position. Thus, the nebulizer automatically cycles aerosol generation in time with the breathing cycle of the patient.

If the patient exhales into the nebulizer, no nebulization occurs since the diverter 60 is in the non-nebulizing position due to the biasing of the membrane 64. Upward travel of the chimney 50 is limited by the cover 21.

During inhalation, some air flow may be provided through the nebulizer in a path through the chimney 50. This air flow into the chamber 14 may be provided from ambient in a path provided through the ports 72, the chimney inlet 56, the chimney passageway 52, and the chimney outlet 58. This air flow may continue during both inhalation when the chimney 50 is in the lower position and exhalation when the chimney is in the higher position. Alternatively, the air flow through the chimney 50 may be stopped or reduced during inhalation when the chimney 50 is in the lower position. Control of the airflow through the nebulizer during inhalation or exhalation may be effected by suitable selections of the dimensions of the chimney inlet 56, the chimney outlet 58, the actuator ports 72, the diverter ring 82, and other components that affect airflow through the chamber, such as any filters.

In the embodiment described above, the membrane 64 provides an elastic triggering threshold that permits cyclical nebulization to occur that coincides with the breathing of the patient. This threshold is set to fall within normal human breathing parameters so that the diverter moves into and out of proximity with the nozzle top as a result of the patient's normal breathing. In one embodiment, this level may be approximately less than or equal to 3.0 cm of water. It can be appreciated that the threshold may be established at different levels to account for different classes of patients. For example, if the nebulizer is designed to be used with infants or neonatals, the elastic threshold of the membrane may be lower than the threshold used for adults. Similarly, a different threshold may be used for geriatric patients. The nebulizer may be used also for veterinary applications, such as equine or canine. In veterinary applications, there may be a relatively wide range of thresholds related to the various sizes of animals. Nebulizers having suitably chosen operating thresholds can be designed for veterinary uses. It is also recognized that the openings into the chamber, such as the opening 56, may affect the operating threshold for nebulization. Thus, the operating threshold of the nebulizer may be made readily adjustable by making the actuator 68 adjustable. Alternatively, the operating threshold may be adjusted by selection of the size of the openings 56 and 72 into the chamber which would also control air entrainment. This would permit the user to adjust the thresholds, if desired. By appropriate adjustment of the operating thresholds, flow control through the nebulizer can be provided. For example, it may be desirable that the patient not inhale or exhale too quickly or too deeply. For adults, a suitable flow rate may be approximately 30-60 liters/minute. The openings into and out of the chamber may be suitably adjusted to provide for these rates.

The nebulizer may be operated manually instead of relying on the breath-actuated feature. To operate the nebulizer manually, the actuator 70 is pressed down toward the cover 21. As mentioned above, the actuator 70 is connected to the chimney 50. Pressing the actuator 70 brings the diverter 60 down into the nebulizing position close to the nozzle 24. Release of the actuator 70 causes the chimney 50 to rise due to the biasing of the membrane 64 thereby causing nebulization to cease.

Figure 4A:
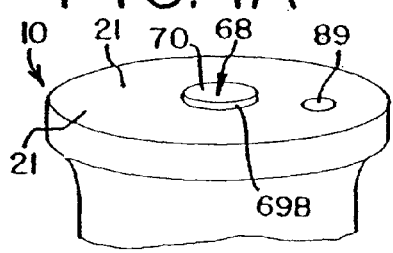
FIG. 4A is perspective view of the top of the nebulizer shown in the inspiration cycle of FIG. 1A.

Referring to FIGS. 4 and 4A, the indicators 69A and 69B provide a convenient way to confirm the operation of the nebulizer. As mentioned above, when the diverter 60 is spaced away from the top of the nozzle 24, no aerosol is being generated. When the diverter 60 is spaced away the actuator 68, the actuator 68, which is connected to the diverter 60 through the chimney 50, is in an upper position and the red indicator 69A on the side of the actuator 68 is visible along the top side 21 of the nebulizer 10, as shown in FIG. 4. When the patient inhales sufficiently to bring the diverter 60 into a lower position, the red indicator 69A on the side of the actuator 68 is withdrawn through the opening 56 in the top side 21 of the nebulizer 10. The red indicator 69A is no longer visible, however, the green indicator 69B, which is located above the red indicator 69A, remains visible at the top 21 of the nebulizer. Thus, a patient or medical attendant can readily determine whether the nebulizer is operating. In embodiments of the nebulizer for children, the actuator and/or indicators can be designed with comic figures.

The breath actuation of the nebulizer is convenient and efficient. By cycling the nebulization of the liquid, the nebulizer can be more efficient thereby reducing the cost of the therapy.

An important advantage follows from the feature of this nebulizer that nebulization can be cycled so as to occur in coordination with a physiological cycle of the patient. Specifically, by nebulizing only during an inhalation, for example, the dosage of medication delivered to the patient can be more accurately delivered and monitored. This enables this embodiment of the nebulizer to provide for dosimetric medication delivery to an extent that has been otherwise unavailable. By limiting the medication delivery to the inhalation cycle of the patient, a dosimetric portion of the medication can be provided.

In addition, the nebulizer 10 provides for high output and uniform nebulization due to the arrangement of the gas and liquid orifices 38 and 46 relative to the diverter 60. The annular configuration of the liquid orifice 46 relative to the gas orifice provides for aerosol generation in a approximately 360.degree. direction. This enables a relatively high and uniform rate of nebulization. The uniformity it enhanced because the nebulization is formed with little or no impaction of liquid against the diverter.

In alternative embodiments of the nebulizer, the cover 12 may include an air filter that covers the air inlet 56. The filter would serve to keep contaminants out of the chamber and deter the escape of nebulized liquid. Such a filter may be removable to permit simple, inexpensive replacement.

In a still further embodiment, the nebulizer may be used in conjunction with an aerosolization spacer, such as an Aerochamber® sold by Trudell Medical Partnership of London, Ontario. The Aerochamber spacer is described in U.S. Pat. No. 4,470,412, the entire disclosure of which is incorporated by reference herein. In this alternative embodiment, the output of the nebulizer would be directed into the inlet of the Aerochamber from which the patient inhales the aerosol through an outlet of the Aerochamber.

Another advantage provided by this embodiment of the nebulizer is that less aerosol is likely to escape to the surrounding environment. This potentially benefits attending care providers who would otherwise be exposed to aerosol medication that is released from nebulizers that generate on a continuous basis.

In a present embodiment, the membrane 64 is biased to keep the chimney in an upper, non-nebulizing position except during inhalation. Thus, in the periods of time between inhalations and exhalations, or if the patient pauses and removes the mouthpiece, nebulizing does not take place. In alternative embodiments, the membrane 64 may bias the chimney downward so that the nebulizer generates an aerosol or nebula except during exhalation. This alternative may not be as efficient as the prior alternative, but may still provide significant advantages over nebulizers that generate aerosol continuously.

In further alternative embodiments of the nebulizer, the gas orifice 38, the gas passageway 34, or a portion thereof, may have a shape that modifies the force of the pressurized gas against the diverter 60. For example, the gas orifice 38 may have a conical shape that facilitates the change of direction of the gas when it is directed against the diverter, so that the force of the gas would not move the diverter away during inhalation thereby helping to direct the gas out into the chamber. In other embodiments, the conical geometry may be varied to tailor gas force and flow.

As mentioned above, the membrane 62 serves as a biasing member that moves the diverter. Preferably, the membrane is constructed of a silicone rubber material. Other materials capable of repetitive flexing, compression or expansion in response to the force of inhaled or exhaled air, such as a spring, or elastic bellows, may also be used. The biasing member is constructed so that it will move the diverter a predetermined distance away from or toward the nozzle during the course of a patient's spontaneous or ventilated breathing.

In a present embodiment, the diverter moves up and down in response to the patient's breathing. However, in alternative embodiments, the nozzle 24 can move instead of the diverter, or alternatively, both the nozzle and the diverter can move. Also, in a present embodiment, the diverter movement is up and down, but in alternative embodiments, the movement can be side to side, rotating, or pivoting. Alternatively, instead of moving diverter into proximity with a gas outlet, in alternative embodiments, the liquid jet or orifice can be moved toward the gas jet or orifice, or is otherwise directed toward the gas jet or orifice, or vice versa. In effect, alternative embodiments contemplate various means of bringing or diverting the gas and liquid streams into proximity in a cyclical basis.

In alternative embodiments of the nebulizer, the liquid orifice may have shapes other than annular. For example, the liquid orifice may be located adjacent to the gas orifice. Alternatively, the liquid orifice may be formed of a series of orifices positioned adjacent or annularly around the gas orifice.

The nebulizer 10 may also be provided with a plurality of support legs (not shown) that are connected around the exterior of the housing 12 and provide support therefore.

In this embodiment, the diverter 50 moves into proximity with the nozzle 24 due to a negative pressure in the chamber 14. However, the pressure variance may also be created by a variance in positive pressure, or a combination of positive and negative pressures.

II. Second Embodiment

Figure 5:
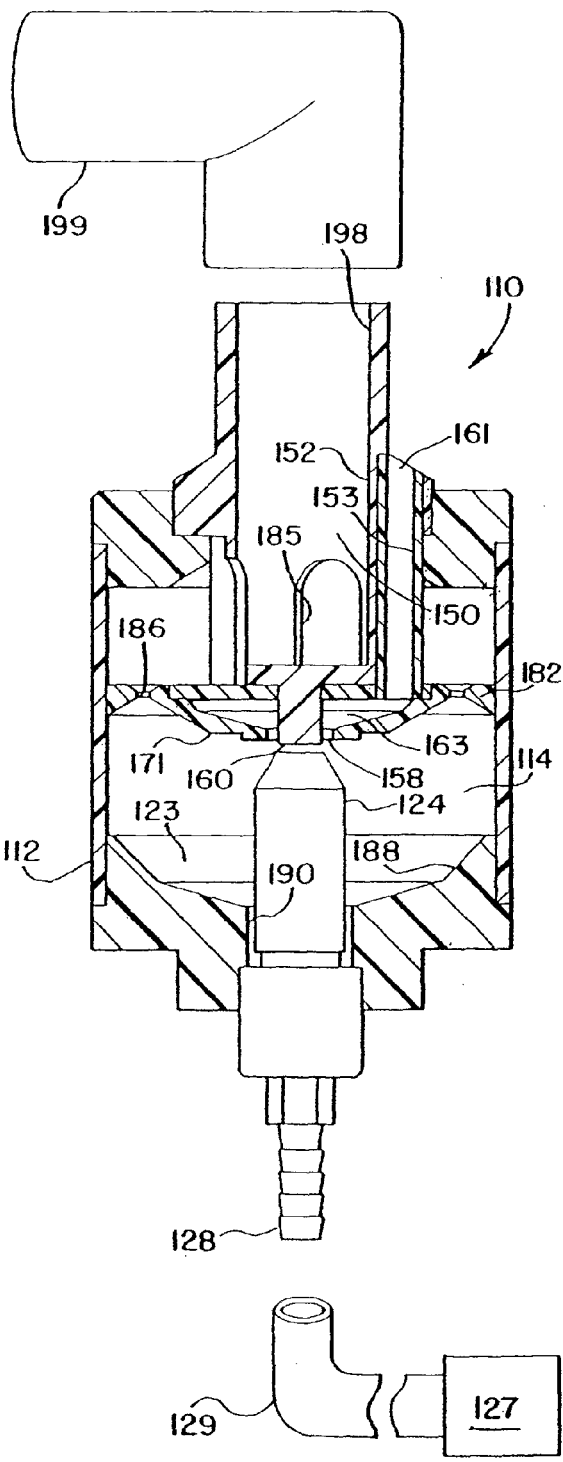
FIG. 5 is a cross sectional view of a second embodiment of the nebulizer of the present invention.

A second embodiment of a nebulizer is shown in FIG. 5. According to this embodiment, a nebulizer 110 has a housing 112 that defines a chamber 114. A lower portion of the chamber 114 serves as a reservoir 123 for holding a liquid to be nebulized. Located in a lower portion of the housing 112 is a nozzle assembly 124. The nozzle assembly 124 may be similar or identical to the nozzle assembly of the first embodiment, described above. Like the first embodiment, a bottom of the nozzle assembly 124 has a fitting 128 that can be connected to a supply of pressured gas 127 by means of conventional tubing 129. Located in the nozzle assembly 124 are inner and outer tubular members that define gas and liquid passageways that exit at gas and liquid orifices at the top of the nozzle assembly 124, as in the first embodiment. Like the first embodiment, the gas and liquid orifices preferably have a concentric arrangement with the liquid orifice having an annular shape encircling the gas outlet orifice. Also, like the first embodiment, in the embodiment of FIG. 5 the reservoir 123 includes a relatively wide, but shallow, primary or upper portion 188 and a relatively narrow, but deep, lower or secondary portion 190.

Although this embodiment is shown without a bell-shaped baffle similar to baffle 74 of the first embodiment, a baffle may be provided in this embodiment. If a baffle were provided in this embodiment, it would have a construction similar to that of the baffle 74 of FIG. 1.

In the embodiment of FIG. 5, a chimney 150 is located in an upper portion of the housing 112. The chimney includes a first internal passageway 152. In this embodiment, the internal passageway 152 of the chimney assembly 150 serves as a chamber outlet 198 from the chamber 114. The outlet connects to a mouthpiece 199, or other suitable means of delivering an aerosol to a patient, such as a mask. A diverter 160 is located at and connected to a lower end of the chimney 150. The diverter 160 is located a predetermined distance from the top of the nozzle assembly 124. In this embodiment, this distance is approximately 0.033 inches. Unlike the first embodiment, the chimney assembly 150 in this embodiment 110 is not movable between upper and lower positions. Instead, the chimney assembly 150 is fixed in position so that the diverter 160 is maintained a suitable distance from the top of the nozzle assembly 124 to generate an aerosol.

In this embodiment, at least one second air passageway 153 is provided. The second air passageway 153 is located adjacent to the first air passageway 152 in the chimney assembly 150. The second air passageway 153 communicates with an inlet opening 161 and a suction chamber 163. The suction chamber 163 is located around a lower end of the chimney assembly 150 and specifically, around the perimeter of the diverter 160. An opening 158 communicates between the suction chamber 163 and the chamber 114 and serves as an air outlet from the aerosol chamber 114 to the suction chamber. As pressurized gas and nebulized liquid flow past the perimeter of the diverter 160, a pressure variance is created that draws air from ambient through the inlet opening 161 through the second passage way 153 into the suction chamber 163. In one embodiment, the pressure variance is a negative pressure, however, the pressure variance may also be created by a variance in positive pressure, or a combination of positive and negative pressures. The suction provided at the opening 158 serves to enhance generation of the aerosol.

A nebulizing enhancement feature provided by the nebulizer 110 relates to the shape of wall 171 around the opening 158. As shown in FIGS. 5 and 6, the shape of the wall 171 includes a first region 173 and a second region 175. The first region 173 is separated from the second region 175 by a step or shoulder 177. The first region 173 and the second region 175 are preferably horizontal, flat surfaces and the shoulder 177 is preferably a vertical surface. The wall 171 also includes a third region 179. The third region 179 is located around the second region 175. The third region 179 is a sloped or angled surface that extends from the second region 175 to a gap 186 formed adjacent to a diverting ring 182.

The shapes of the first, second and third regions 173, 175 and 177 affect the air flow in the chamber from the diverter. The relative sizes and shapes may be varied to enhance particle size generation and uniformity. An alternative embodiment of the wall 171 and regions 173, 175, and 177 is shown in FIG. 7. In the embodiment of the wall 171A shown in FIG. 7, the relative sizes of the first region 173A, second region 175A, and third region 177A are modified relative to those in the embodiment of FIG. 6. These sizes are varied to affect the size and uniformity of the particle distribution of the nebula or aerosol.

Referring again to FIG. 5, located in a wall of the chimney 150 is at least one, and preferably a plurality of openings 185. Openings 185 communicate between the chamber 114 and the first air passageway 152 of the chimney assembly 150.

Referring to FIGS. 5 and 8, a diverting ring 182 may be provided in the chamber 114 to reduce the presence of large droplets and help make the aerosol delivered to the patient more uniform. As mentioned above in connection with the first embodiment, the diverting ring provides this function, in part, by limiting the migration of droplets on the inside wall of the nebulizer housing. In addition, by forming a barrier on the inside wall of the housing, the diverting ring forces the nebulized aerosol to travel along a relatively non-linear path to move from the lower part to the upper part of the chamber and out the mouthpiece.

Referring to FIG. 5, to operate the nebulizer 110, a suitable amount of liquid medicine is placed in reservoir of the chamber 114. The outlet 198 is connected to the mouthpiece 199 in a suitable manner. The source of pressurized gas 127 is connected to the fitting 128. The flow of gas from the top of the nozzle assembly 124 is directed by the diverter 160 across the annular liquid orifice surrounding the gas orifice causing the generation of an aerosol from the liquid in the reservoir. The aerosol is generated in a 360.degree. direction into the chamber 114 around the nozzle 124 and diverter 160.

An air flow path is established into the chamber 114 from the inlet 161. The gas provided by the source 127 also supplements the air supply into the chamber 114. Air flows into the chamber through the second passageway 153 through the suction chamber 163 and opening 158. Air flow laden with aerosolized liquid from the chamber 114 travels past the gap 186, through the opening 185, into the first air passageway 152, and out from the outlet opening 198 to the mouthpiece 199 or face mask. In this embodiment, nebulization may proceed continuously, or may be cycled by other means, such as cycling of the gas supply.

Alternative embodiments of the diverting ring arrangement are shown in FIGS. 9 and 10. In FIG. 9, the diverting ring 182A extends further toward the chimney 150 almost overlapping an edge 183A at the bottom 150A of the chimney 150. This arrangement provides an even more tortuous pathway for the aerosol than the embodiment shown in FIG. 8. The embodiment of FIG. 8 may provide an even more uniform particle distribution. In FIG. 10, the passageway between the diverting ring 182B and the bottom 150B of the chimney is extended thereby providing a longer pathway of a narrow dimension. The embodiment of FIG. 10 may provide an even more uniform particle distribution than the embodiments of FIGS. 8 or 9.

III. Third Embodiment

Figure 11:
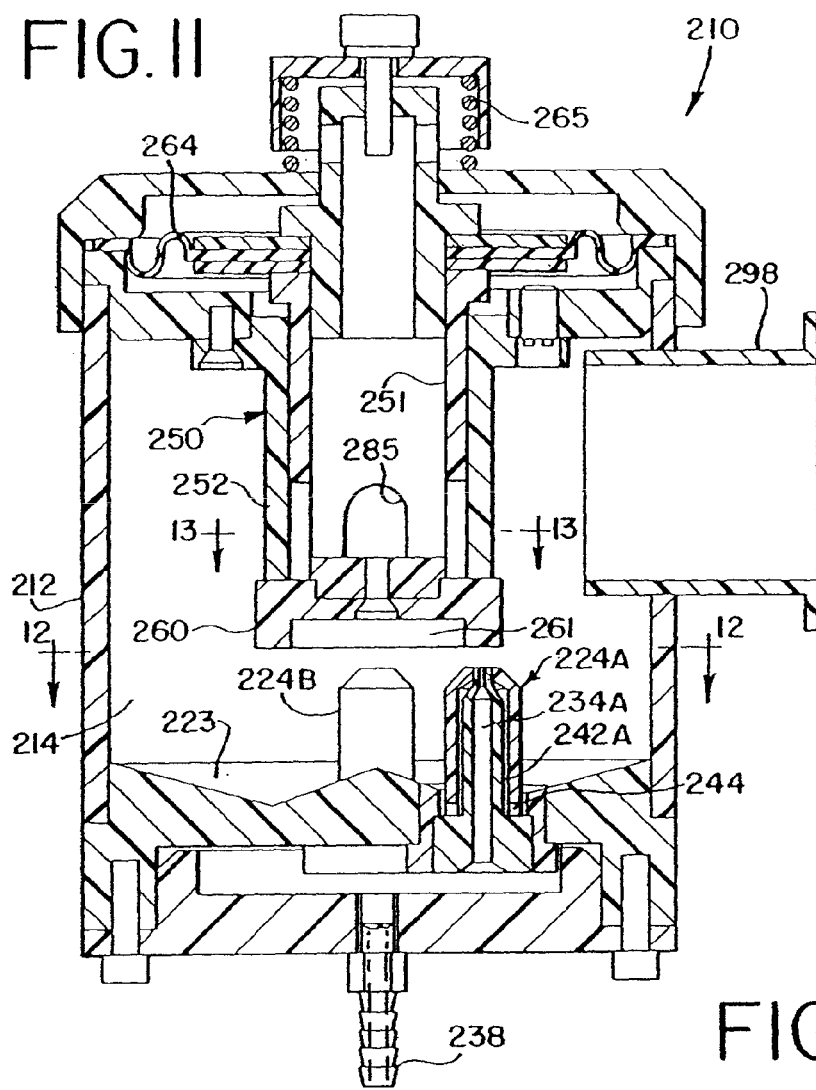
FIG. 11 is a cross sectional view of a third embodiment of the nebulizer of the present invention.
Figure 13:
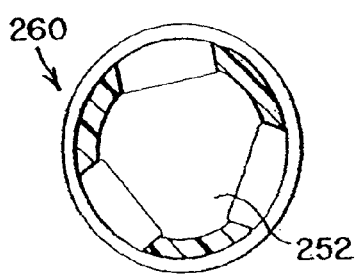
FIG. 13 is a cross sectional view of the embodiment of FIG. 11 taken along line 13-13'.
Figure 12:
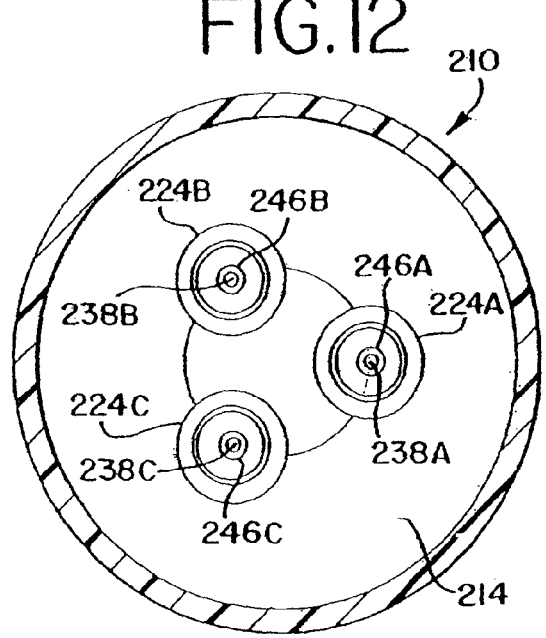
FIG. 12 is a top view of the embodiment nozzle assembly of FIG. 11.

A nebulizer 210 according to another embodiment of the invention is shown in FIGS. 11-13. The nebulizer 210 is similar to the previous embodiments of the nebulizers discussed above. The nebulizer 210 includes a housing 212 defining a chamber 214. In the embodiment of FIG. 11, the housing 212 is relatively larger than the housings of the previous embodiments. For example, the housing 212 may have a height of approximately 11 cm (4.33 in.) and a diameter of approximately 9 cm (3.54 in.). This enables the nebulizer 210 to hold a correspondingly larger volume of liquid and aerosol. A large size nebulizer, such as shown in FIG. 11, may be suitable for certain veterinary applications such as for horses, cattle, dogs, etc. A larger size nebulizer may also be used with humans for uses such as sputum induction.

A fitting 238 connects to a pressurized gas supply (not shown) and an outlet 298 provides nebulized medicine from the chamber 214 to the patient. The outlet 298 may connect to a mouthpiece, mask, or ventilator, as appropriate. Like the first described embodiment, the nebulizer 210 has a movable chimney 250. In the chamber 214 of the nebulizer 210, there are a plurality of nozzle assemblies 224A, 224B, and 224C. Each of these nozzle assemblies may be similar to the nozzle assembly 24 of the first embodiment. Each of the nozzle assemblies includes a gas supply passageway, such as 234A, and an annular liquid supply passageway, such as 242A. At the top ends of each of the nozzles 224A, 224B, and 224C, the gas passageways of each communicate with gas outlet orifices 238A, 238B, and 238C, respectively and the liquid passageways of each communicate with liquid outlet orifices 246A, 246B, and 246C. The liquid inlets 244 into each of the nozzles assemblies communicate in common with a reservoir 223 formed at the bottom of the chamber 214.

Located at the bottom of chimney is a diverter 260. The diverter 260 may be formed of a single face or surface, or may be formed of multiple faces or surfaces that are aligned with the multiple nozzle assemblies 224A-224C, or alternatively, the diverter may be formed as a ring. Further, there may be provided multiple diverters. In a preferred embodiment, there is a space or gap 261 formed centrally in the bottom of the diverter 260 to permit aerosol generation in 360.degree. around each of the nozzles.

A membrane 264 may be located at the top of the chimney 250 to provide a biasing function as in the embodiment of FIG. 1. Due to the larger size and weight of the chimney assembly 250 in the embodiment of FIG. 11 relative to the embodiment of FIG. 1, a biasing member 265 such as a spring may be provided in substitution for or in addition to the membrane 264. The spring or other biasing member 265 may be connected to the top of the chimney assembly 250.

The nebulizer 210 is operated in a manner similar to the nebulizer shown in FIG. 1. Like the nebulizer shown in FIG. 1, the nebulizer 210 in FIG. 11 is breath- or pressure-actuated. After a suitable liquid is stored in the housing 212, the generation of a nebula or aerosol will cycle with the cyclic decrease of pressure in the chamber 214. The decrease of pressure may be caused by inhalation by the patient, or by action of ventilator. As in the first embodiment, nebulization will cease upon exhalation or in the absence of inhalation.

Because the nebulizer 210 has multiple nozzles 224A-C, a large amount of liquid can be nebulized quickly. Since the single diverter or connected multiple diverters move in unison toward the multiple nozzles with the patient's inhalation, the cycling of nebulization is coordinated among all the nozzles.

As in the previous embodiments, the annular shape of each of the liquid orifices provides for a high nebulization generation rate. Although the embodiment of FIGS. 11-13 shows three nozzles, there can be any number of multiple nozzles, such as two, four, five, etc.

In an alternative embodiment, the diverter 260 is rotatable relative to the body 252 of the chimney 150. The diverter 260 may include appropriate vanes, channels or a propeller, that captures some of the pressurized gas flow and causes the diverter 260 to rotate inside the housing 212. Rotation of the diverter 260 may be used to improve mixing of the aerosol inside the chamber.

This embodiment may also include a bell-shaped baffle as shown in the first embodiment.

IV. Fourth Embodiment

Figure 14:
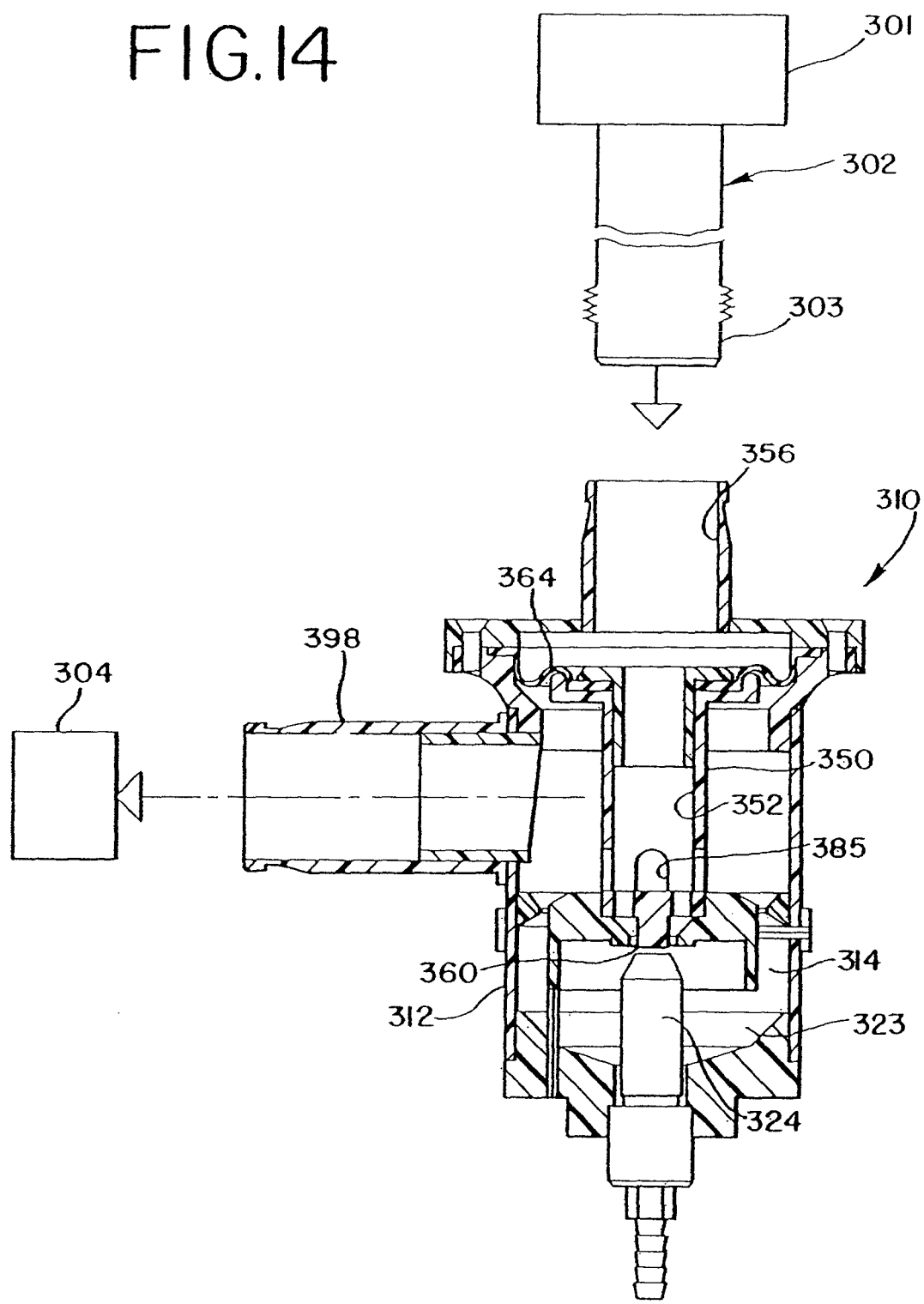
FIG. 14 is a cross sectional view of a fourth embodiment of the nebulizer of the present invention.

FIG. 14 shows a fourth embodiment of a nebulizer of the present invention. This embodiment 310 of the nebulizer is adapted for use with a ventilator circuit 301. The ventilator circuit 301 includes an inspiratory airflow passageway 302 that delivers air from the ventilator to the patient. This embodiment of the nebulizer 310 is located in the inspiratory airflow passageway 302 connected between a first length of inspiratory tubing 303 that delivers air from the ventilator circuit 301 and a second length 304 that delivers air to the patient. The second length of inspiratory tubing 304 may connect to the patient by means of a mask, endotracheal tube, etc.

Like the embodiment of FIG. 1, the embodiment of the nebulizer in FIG. 14 is pressure- or breath-actuated. Accordingly, the nebulizer 310 produces an aerosol in a cyclical manner in coordination with the breathing or ventilation of the patient. The nebulizer 310 has a housing 312 defining a chamber 314. A nozzle assembly 324 extends up from the bottom of the chamber 314. Pressurized gas is delivered from a gas orifice at the top end of the nozzle assembly 324 and liquid from a reservoir 323 at the bottom of the chamber 314 is drawn up to a liquid orifice also located at the top end of the nozzle assembly 324 as in the first embodiment. A chimney assembly 350 extends down from a top of the housing 312. The chimney 350 connects to the housing by means of a flexible, resilient membrane 364. A diverter 360 is located at the bottom of the chimney assembly 350 directly opposite from the gas and liquid orifices at the top of the nozzle assembly 324. An inlet 356 of the chimney 350 connects to the length of inspiration tubing 303 from the ventilator circuit 301. The inlet 356 communicates with an internal passageway 352 of the chimney assembly 350. Inspiratory gas from the ventilator 301 enters the nebulizer 310 via the chimney inlet 356, passes through the passageway 352 of the chimney assembly 350, and passes into the nebulizer chamber 314 through the openings 385 located in the wall of the chimney 350. The inspired gas exits the nebulizer chamber 314 via an outlet 398. The outlet 398 connects to the second length of inspiratory tubing 304 which in turn connects to an endotracheal tube, a mask, or other means (not shown). This embodiment may also include a bell-shaped baffle as shown in the first embodiment.

In the embodiment of FIG. 14, the normal operation of the ventilator circuit 301 causes a sufficient change in the pressure in the nebulizer 310 to induce the chimney assembly 350 to move into and out of proximity with the nozzle assembly 324. Accordingly, during an inspiration cycle, the chimney assembly 350, including the diverter 360, will be brought into proximity with the top of the nozzle assembly 324 causing nebulization of the liquid (as described above in connection with the first embodiment). During an expiratory phase of the ventilator 301, the diverter 350 is positioned away from the nozzle assembly 324 thereby causing nebulization to stop. Nebulization cycles automatically in synchronism with the operation of the ventilator. No extra connection is required beyond that necessary to withdraw the aerosol from the chamber 314 of the nebulizer 310 into the inspiratory tubing of the ventilator circuit.

V. Fifth Embodiment

Figure 15:
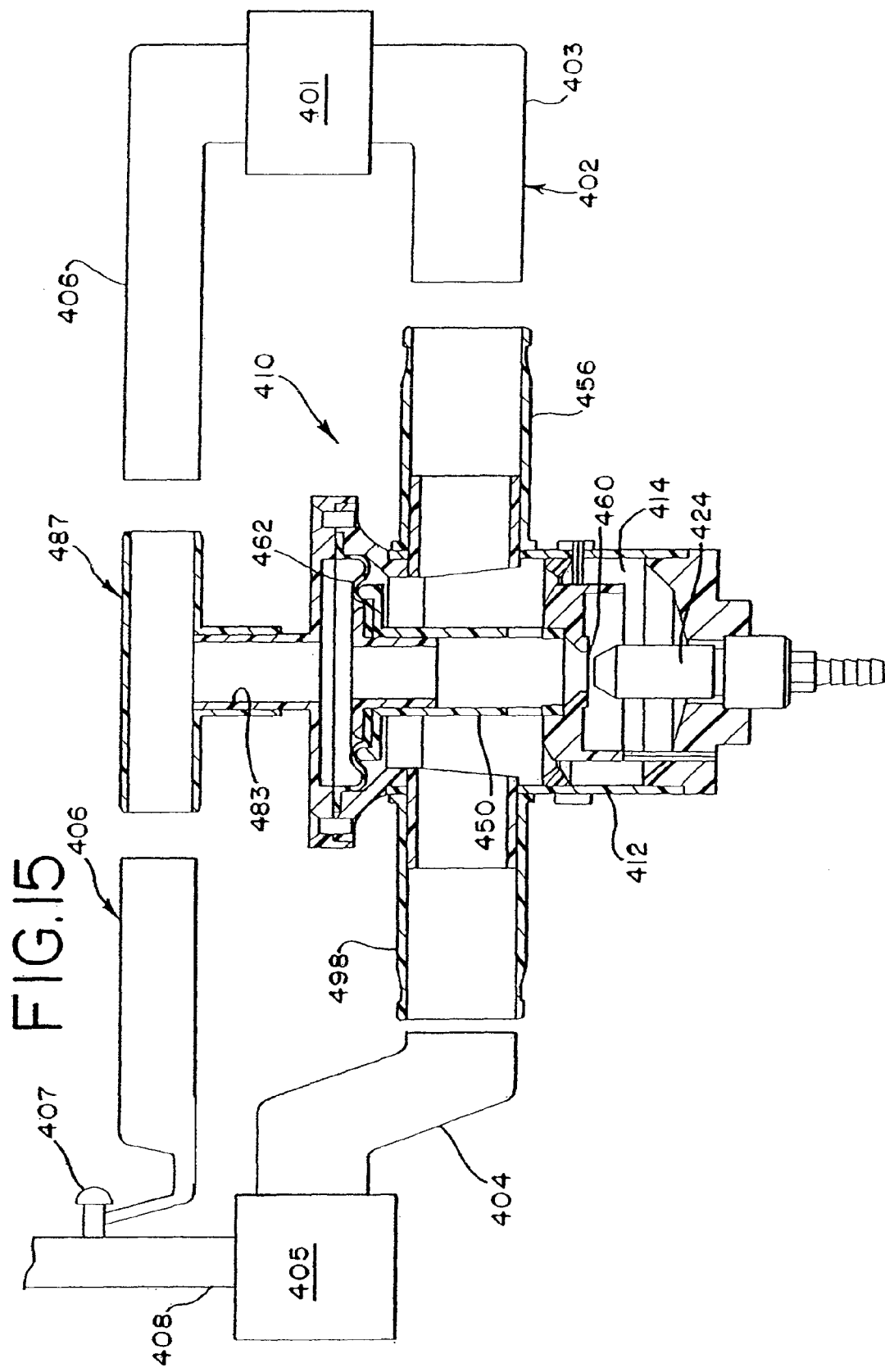
FIG. 15 is a cross sectional view of a fifth embodiment of the nebulizer of the present invention.

FIG. 15 shows a fifth embodiment 410 of the nebulizer of the present invention. Like the previous embodiment, the nebulizer 410 in FIG. 15 is adapted for use in a ventilator circuit and produces an aerosol in a cyclical manner in coordination with operation of the ventilator and/or the breathing of the patient.

A ventilator circuit 401 has an inspiratory passageway 402 that is formed of a first length of tubing 403 that connects to the ventilator 401 and a second length of tubing 404 that connects to a mask 405, or endotracheal tube, and so on, associated with the patient. The ventilator circuit 401 also includes an exhalation valve pressure line 406. This exhalation valve pressure line 406 connects to an exhalation valve 407 associated with an expiratory passageway 408. During ventilation of the patient, pressured gas is delivered in the exhalation valve pressure line 406 to the exhalation valve 407 to assist in the cycling of ventilation of the patient.

The nebulizer 410 has a housing 412 defining a chamber 414, and includes a nozzle assembly 424, a flexible, resilient membrane 462, and a diverter 460, arranged generally as in the previously described embodiment. Instead of a chimney, the nebulizer 410 has a post 450 to which the diverter 460 is connected. Unlike a chimney, the post 450 does not include air openings or an internal air passageway. The diverter 460 is connected to a bottom side of the post directly adjacent from the top of the nozzle assembly 424. The embodiment of FIG. 15 also differs from the previous embodiment in the manner that the ventilator circuit 401 is connected to the nebulizer 410 and the manner that the ventilator circuit 401 causes the nebulizer 410 to cycle nebulization. This embodiment may also include a bell-shaped baffle as shown in the first embodiment.

In FIG. 15, the nebulizer housing 412 includes an inlet 456 into the chamber 414. The inlet 456 connects to the first section 403 of inspiratory tubing 402 from the ventilator circuit 401. The nebulizer housing 412 also includes an outlet 498 from the chamber 414. The outlet 498 connects to the second section 404 of inspiratory tubing that leads to a conventional device 405, e.g. an endotracheal tube or mask, from which the patient receives the inspiratory flow from the ventilator 401 including the aerosol from the nebulizer 410.

Located across the membrane 462 from the nebulization chamber 414 is a passageway 483. The passageway 483 connects to the exhalation valve pressure line 406 of the ventilator circuit 401 by a suitable means, such as a tee 487. Because the ventilator 401 cycles air to and from the patient, air flows in the exhalation valve pressure line 406 in a cyclic manner to operate the exhalation valve 407. This air flow in the exhalation valve pressure line 406 causes a pressure differences with the air in the chamber 414. The membrane 462 is positioned across the inspiratory flow passageway 402 and the exhalation valve pressure line 406 and therefore senses the pressure differential across these two passageways. As in the previous embodiment, the diverter 460 is brought into proximity with the top of the nozzle assembly 424 during the inspiratory phase of the ventilator and brought out of proximity with the top of the nozzle assembly 424 during the expiratory phase of the ventilator. Accordingly, nebulization occurs during the inspiratory phase and not during the expiratory phase.

VI. Sixth Embodiment

FIG. 16 shows a sixth embodiment 510 of the nebulizer of the present invention. This embodiment is similar to the embodiment of the nebulizer 110 in FIG. 15. The nebulizer 510 includes a housing 512 defining a chamber 514. The chamber 514 has an inlet 528 connected to a source of pressurized gas 527 and an outlet 598 connected to a tubing 599, or similar structure, such as a mouthpiece, etc., that leads to the patient 596 and from which the patient can inhale air and aerosol. Like the embodiment of FIG. 5, the nebulizer 510 of FIG. 16 may also include an inlet for air entrainment 562. As in the other embodiment, liquid and gas outlets (not shown) located at the top of a nozzle 524 directly adjacent a diverter 560 dispense an aerosol into the chamber 514.

The embodiment of the nebulizer 510 includes a breath-actuation feature that enables the nebulizer to generate a nebula in cyclic manner in coordination with a physiological cycle of the patient. In the embodiment of FIG. 15, the breath-actuation feature is external of the nebulizer housing 512. The breath-actuation feature includes a valve 569 or other metering device located in-line with the inlet tubing 529 that provides the pressurized gas from the source 527 to the nebulizer inlet 528. A tubing 567 connects from the outlet tubing 599 to the inlet tubing 529. The tubing 567 enables the valve 569 to sense the pressure in the outlet tubing 599. In one embodiment, the tubing 567 may be conventional tubing and the valve 569 senses the pressure through the tubing 567. The valve 569 is adapted to open and close the delivery of pressurized gas to the nebulizer 510 in coordination with the changes in the pressure in the outlet 599 as sensed via the tubing 567. Specifically, upon inhalation, the pressure in the inlet 599 and the connecting tubing 567 will be lower, and the valve 569 will open to allow pressurized gas to be delivered to the nebulizer 510 thereby causing nebulization to occur. After inhalation, the pressure in the patient outlet 599 and the connecting tubing 567 rises, and the valve closes thereby causing nebulization to cease. In this manner, the embodiment of FIG. 16 can provide similar breath-actuation features as the other embodiments discussed above. The tubing 567 and valve 569 may be either re-usable or disposable and may be used with a nebulizer 510 as shown in FIG. 16, or may be used with other types of nebulizers. The tubing 567 and valve 569 could also be used with vaporizers that are used for providing humidification for ventilated patients. Such vaporizers are used with prefilled bags of sterilized water, and the tubing 567 and valve 569 would provide adjustable air entrainment of vapor.

VII. Seventh Embodiment

Figure 17A:
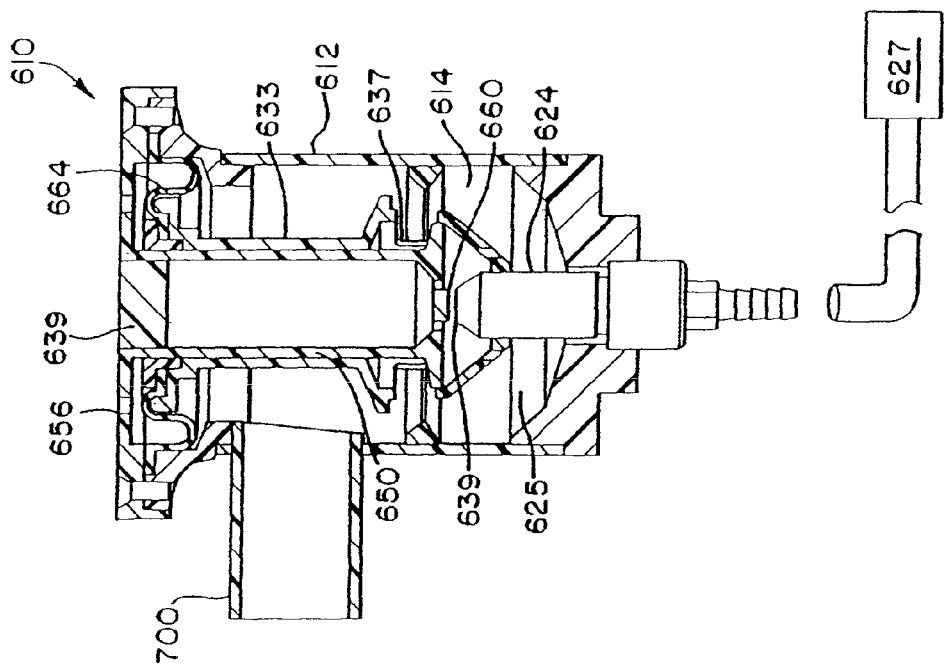
FIGS. 17A and 17B shows cross sectional views of a seventh embodiment of the present invention.
Figure 17B:
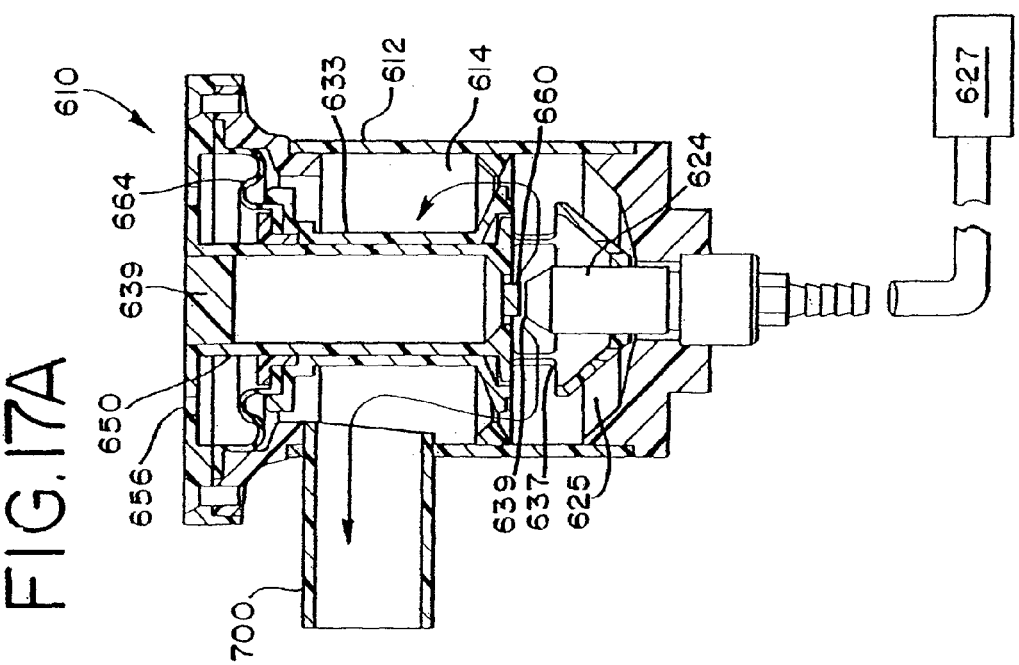

FIGS. 17A and 17B show a seventh embodiment 610 of the nebulizer of the present invention. This embodiment is similar to the previous embodiments wherein a housing 612 defines a chamber 614 for holding and aerosolizing a liquid 625 by means of a pressured gas supply 627. In this embodiment, a top end of a diverter assembly post 650 is connected to the top side of the housing so that the bottom surface 660 of the diverter post 650 is located at a fixed distance, e.g. 0.033 inches, from a top 639 of a nozzle assembly 624. As in the previous embodiments, a gas orifice and a liquid orifice (not shown) are located at the top of the nozzle assembly 624. The liquid orifice may be ring-shaped and concentric with the gas orifice, or alternatively, the orifices may be side by side. A mouthpiece 700 permits the withdrawal of aerosol and air from the chamber 614. A flexible diaphragm 664 is located in an upper region of the nebulizer chamber 614 and forms a boundary between the inside of the chamber and the ambient outside. One or more air inlet ports 656 are located on a top side of the housing 612. A filter 639 is located at the top of the diverter post 650.

A cylindrical shield or collecting surface 633 is connected to the flexible diaphragm 664 and extends downward into the chamber 614 over the lower portion of the diverter post 650 and the upper portion of the nozzle assembly 624. The shield 633 has an inside diameter larger than the outside diameters of the diverter post 650 and the nozzle assembly 624 so that it can readily shift relative to these parts. One or more windows 637 are located in the wall of the shield 633. The windows 637 are located in the wall of the cylindrical shield 633 such that when the diaphragm 664 is in an upper position (as shown in FIG. 17B) the window 637 is not aligned with the gap between nozzle 624 and the diverter 660. When the shield 633 is in this upper position, aerosol particles generated by the flow of pressured gas across the liquid orifice impact upon the inside wall of the cylindrical shield 633 and tend to form into droplets that fall back into the reservoir. In addition or alternatively, depending on the specific dimensions, the shield 633 may impede the flow of gas from the pressurized gas orifice across the liquid orifice to the extent that there is insufficient vacuum to draw the liquid out of the liquid orifice. In any event, the production of aerosol particles into the chamber 614 is reduced. However, when air is withdrawn from the chamber 614, such as when a patient inhales through the mouthpiece 700, a decrease in pressure inside the chamber 614 causes the diaphragm 664 to flex downward (as shown in FIG. 17A). This causes the cylindrical shield 633 to shift into a lower position. When the shield 633 is in a lower position, the window 637 is aligned with the gap between the nozzle 624 and the diverter 660 thereby permitting aerosol generated from the liquid orifice to escape into the chamber 614 from which it can be inhaled by the patient.

The above embodiments of the nebulizer have been described for use in medical or therapeutic applications. It is noted that the principles of the invention disclosed herein may have applicability to other usages, such as industrial, manufacturing, or automotive (e.g. carburetors).

It is intended that the foregoing detailed description be regarded as illustrative rather than limiting, and that it be understood that the following claims, including all equivalents, are intended to define the scope of this invention.

The invention claimed is:

1. An apparatus for aerosol delivery comprising:
a housing defining a chamber for holding an aerosol;
an air inlet in communication with the chamber, the air inlet configured to permit a flow of air into the chamber;
an air outlet in communication with the chamber, the air outlet configured to permit the aerosol to be withdrawn from the chamber; and
an indicator operatively connected with the chamber, the indicator mechanically moveable in response to inhalation of a patient and in response to exhalation during a breathing cycle of the patient independent of a level of any liquid in the chamber, wherein the indicator comprises a visible characteristic, maintains a same size during the breathing cycle, and is positioned away from an inspiration path of the aerosol.

2. The apparatus of claim 1, wherein the indicator is positioned away from the air outlet.

3. The apparatus of claim 1, further comprising a mouthpiece in communication with the air outlet.

4. The apparatus of claim 3, wherein the indicator is positioned away from the mouthpiece.

5. The apparatus of claim 1, wherein the indicator comprises a figure.

6. The apparatus of claim 1, wherein the indicator is configured to cycle between a first position and a second position in response to the breathing cycle of the patient.

7. The apparatus of claim 1, further comprising a mouthpiece in communication with the outlet means.

8. The apparatus of claim 7, wherein the means for visually indicating is positioned away from the mouthpiece.

9. The apparatus of claim 7, wherein the indicator comprises a figure.

10. The apparatus of claim 7, wherein the means for visually indicating is configured to cycle between a first position and a second position in response to the breathing cycle of the patient.

11. The apparatus of claim 1, wherein the chamber comprises a liquid.

12. The apparatus of claim 1, wherein the indicator is movable between a first position and a second position, and wherein the indicator maintains a same shape regardless of position.

13. An apparatus for aerosol delivery comprising:
means for holding an aerosol;
inlet means for permitting a flow of air into the means for holding the aerosol;
outlet means for permitting the aerosol to be withdrawn from the means for holding the aerosol; and
means for visually indicating to a patient a breathing cycle of the patient, the means for visually indicating having a fixed size, operatively connected with the means for holding the aerosol, mechanically moveable in response to inhalation of the patient and in response to exhalation of the patient during the breathing cycle independent of a level of any liquid in the means for holding an aerosol and positioned away from an inspiration path of the aerosol.

14. The apparatus of claim 13, wherein the means for visually indicating is positioned away from the outlet means.

15. The apparatus of claim 13, wherein means for holding an aerosol comprises a liquid.

16. The apparatus of claim 13, wherein the means for visually indicating to a patient a breathing cycle of the patient is configured for movement relative to the means for holding the aerosol and configured to maintain a same shape regardless of a position relative to the means for holding the aerosol.

17. A method for delivering an aerosol from an aerosol delivery apparatus, the method comprising:
supplying the aerosol in a chamber of the aerosol delivery apparatus;
receiving a flow of air into the chamber during inhalation by a patient;
supplying the aerosol along an inspiration path in the aerosol delivery apparatus to an outlet in communication with the chamber during inhalation by the patient; and
visually indicating to the patient a breathing cycle of the patient with a fixed-size indicator that is associated with the aerosol delivery apparatus, positioned away from the inspiration path of the aerosol and mechanically movable in response to inhalation of the patient and in response to exhalation of the patient during the breathing cycle independent of a level of any liquid in the chamber.

18. The method of claim 17, wherein visually indicating comprises moving the indicator in response to the breathing cycle of the patient.

19. The method of claim 17, wherein visually indicating comprises cycling the indicator between a first position and a second position in response to the breathing cycle of the patient.

20. The method of claim 17, wherein the indicator comprises a figure.

* * * * *